(12) United States Patent
Nolan et al.

(10) Patent No.: US 10,561,510 B2
(45) Date of Patent: Feb. 18, 2020

(54) CUSTOMIZING THE ELUTION PROFILE OF A STENT

(71) Applicant: Medtronic Vascular, Inc., Santa Rosa, CA (US)

(72) Inventors: Shane Nolan, Clare (IE); David Hobbins, Galway (IE); Michael Sayers, Limerick (IE); Eamon Keane, Galway (IE); Brian Dowling, Garristown (IE); Jonathan Cope, Santa Rosa, CA (US); Conor O'Donovan, Galway (IE); Risa Egerter, Galway (IE); Lana Woolley, Galway (IE); Marc Anderson, Galway (IE)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 212 days.

(21) Appl. No.: 15/617,743

(22) Filed: Jun. 8, 2017

(65) Prior Publication Data

US 2017/0354520 A1  Dec. 14, 2017

Related U.S. Application Data

(60) Provisional application No. 62/348,495, filed on Jun. 10, 2016.

(51) Int. Cl.
*A61F 2/915* (2013.01)
*A61F 2/89* (2013.01)
(Continued)

(52) U.S. Cl.
CPC ............... *A61F 2/915* (2013.01); *A61F 2/89* (2013.01); *A61F 2/958* (2013.01); *A61M 31/002* (2013.01);
(Continued)

(58) Field of Classification Search
CPC ............... A61F 2/00; A61F 2/915; B65B 1/04
(Continued)

(56) References Cited

U.S. PATENT DOCUMENTS 4,539,226 A   9/1985  Paek et al.
4,886,062 A   12/1989 Wiktor
(Continued)

FOREIGN PATENT DOCUMENTS

EP     1891995 A1    2/2008
WO     1998/23228 A1  6/1998
(Continued)

OTHER PUBLICATIONS

U.S. Appl. No. 61/244,049, filed Sep. 20, 2009, Thompson et al.
(Continued)

*Primary Examiner* — Dah-Wei D. Yuan
*Assistant Examiner* — Andrew J Bowman
(74) *Attorney, Agent, or Firm* — Medler Ferro Woodhouse & Mills PLLC

(57) ABSTRACT

Methods and apparatus are disclosed for customizing an elution profile of a stent after manufacture of the stent has been completed. The stent includes a plurality of side ports for eluting a drug formulation within a lumenal space of a hollow strut that forms the stent. An effective diameter of at least one side port of the plurality of side ports of the stent is modified in order to customize an elution profile of the stent. In an embodiment hereof, the plurality of side ports are completely blocked or plugged with a filler material during the manufacture of the stent and at least a portion of the filler material is removed to increase an effective diameter of at least one side port of the plurality of side ports of the stent in order to customize an elution profile of the stent. In another embodiment hereof, the plurality of side ports are open following the manufacture of the stent and at least one
(Continued)

side port of the plurality of side ports of the stent is at least partially filled with a filler material to decrease the effective diameter of the at least one side port in order to customize an elution profile of the stent. In another embodiment hereof, the stent is soaked within a liquid to remove at least a portion of the drug formulation from the lumenal space of the hollow strut to thereby customize an elution profile of the stent.

20 Claims, 13 Drawing Sheets

(51) Int. Cl.
*A61F 2/958* (2013.01)
*A61M 31/00* (2006.01)
(52) U.S. Cl.
CPC ............ *A61F 2002/91575* (2013.01); *A61F 2210/0004* (2013.01); *A61F 2240/002* (2013.01); *A61F 2250/0068* (2013.01); *A61M 2205/04* (2013.01)
(58) Field of Classification Search
USPC ................................................ 424/426; 141/1
See application file for complete search history.

(56) References Cited

U.S. PATENT DOCUMENTS

| | | | |
|---|---|---|---|
| 5,019,090 A | 5/1991 | Pinchuk | |
| 5,133,732 A | 7/1992 | Wiktor | |
| 5,458,639 A | 10/1995 | Tsukashima et al. | |
| 5,713,949 A | 2/1998 | Jayaraman | |
| 5,782,903 A | 7/1998 | Wiktor | |
| 5,891,507 A | 4/1999 | Jayaraman | |
| 6,136,023 A | 10/2000 | Boyle | |
| 6,203,551 B1 | 3/2001 | Wu | |
| 6,368,658 B1 | 4/2002 | Schwarz et al. | |
| 6,500,147 B2 | 12/2002 | Omaleki et al. | |
| 6,517,889 B1 | 2/2003 | Jayaraman | |
| 6,554,795 B2 | 4/2003 | Bagaoisan et al. | |
| 6,736,827 B1 | 5/2004 | McAndrew et al. | |
| 6,743,462 B1 | 6/2004 | Pacetti | |
| 7,563,324 B1 | 7/2009 | Chen et al. | |
| 7,901,726 B2 | 3/2011 | McMorrow et al. | |
| 8,291,854 B2 | 10/2012 | Behnisch et al. | |
| 8,381,774 B2 | 2/2013 | Mitchell et al. | |
| 8,518,490 B2 | 8/2013 | Ito et al. | |
| 8,668,732 B2 | 3/2014 | Scheuermann et al. | |
| 8,828,474 B2 | 9/2014 | Mitchell et al. | |
| 8,840,660 B2 | 9/2014 | Weber | |
| 9,114,032 B1 | 8/2015 | Pulugurtha | |
| 2004/0200729 A1 | 10/2004 | Boulais et al. | |
| 2005/0010282 A1 | 1/2005 | Thornton et al. | |
| 2005/0038504 A1 | 2/2005 | Halleriet et al. | |
| 2005/0074544 A1 | 4/2005 | Pacetti et al. | |
| 2005/0079274 A1 | 4/2005 | Palasis et al. | |
| 2005/0186241 A1 | 8/2005 | Boyle et al. | |
| 2006/0171990 A1* | 8/2006 | Asgari | A61K 9/0024 424/426 |
| 2007/0259102 A1 | 11/2007 | McNiven et al. | |
| 2008/0152944 A1 | 6/2008 | Bonini et al. | |
| 2008/0208310 A1 | 8/2008 | McDermott et al. | |
| 2008/0233267 A1 | 9/2008 | Berglund | |
| 2009/0035351 A1 | 2/2009 | Berglund et al. | |
| 2009/0093871 A1 | 4/2009 | Rea et al. | |
| 2009/0143855 A1 | 6/2009 | Weber et al. | |
| 2010/0018602 A1 | 1/2010 | Chappa | |
| 2010/0068404 A1 | 3/2010 | Wang et al. | |
| 2011/0008405 A1 | 1/2011 | Birdsall et al. | |
| 2011/0034992 A1 | 2/2011 | Papp | |
| 2011/0066227 A1 | 3/2011 | Meyer et al. | |
| 2011/0067778 A1* | 3/2011 | Mitchell | A61L 31/16 141/1 |
| 2011/0070357 A1 | 3/2011 | Mitchell et al. | |
| 2011/0264187 A1 | 10/2011 | Melder | |
| 2012/0067008 A1 | 3/2012 | Bienvenu | |
| 2012/0067454 A1 | 3/2012 | Melder | |
| 2012/0070562 A1 | 3/2012 | Avelar et al. | |
| 2012/0216907 A1 | 8/2012 | Pacetti | |
| 2013/0274867 A1 | 10/2013 | Bienvenu et al. | |
| 2014/0163664 A1 | 6/2014 | Goldsmith | |
| 2014/0295093 A1 | 10/2014 | Hirao | |

FOREIGN PATENT DOCUMENTS

| | | |
|---|---|---|
| WO | WO2004/091686 | 10/2004 |
| WO | 2008/134493 A1 | 11/2008 |
| WO | WO2011/008896 | 1/2011 |
| WO | WO2012/036929 | 3/2012 |

OTHER PUBLICATIONS

U.S. Appl. No. 61/244,050, filed Sep. 20, 2009, Silver et al.
U.S. Appl. No. 15/491,138, filed Apr. 19, 2017, Mitchell et al.
U.S. Appl. No. 15/491,170, filed Apr. 19, 2017, Mitchell et al.
Kim et al. "Electrically Controlled Hydrophobicity in a Surface Modified Nanoporous Carbon" Applied Physics Letters 98, 053106 (2011).
Vallet et al. "Electrowetting of Water and Aqueous Solutions on Poly(ethylene Terephthalate) Insulating Films" Polymer vol. 37, No. 12, pp. 2465-2470, 1996.
PCT/US2017/036604, The International Search Report and the Written Opinion of the International Searching Authority, dated Sep. 8, 2017, 14pgs.
PCT/US2017/036607, The International Search Report and the Written Opinion of the International Searching Authority, dated Sep. 11, 2017, 14pgs.

* cited by examiner

CUSTOMIZING THE ELUTION PROFILE OF A STENT

CROSS-REFERENCE TO RELATED APPLICATIONS

This application claims the benefit under 35 U.S.C. § 119(e) of the filing date of U.S. Provisional Application No. 62/348,495, filed Jun. 10, 2016, the contents of which are incorporated by reference herein in their entirety.

FIELD OF THE INVENTION

The invention relates generally to implantable medical devices that release a therapeutic substance or drug, and more particularly to methods of and apparatuses for customizing or tailoring an elution rate or profile of the implantable medical devices.

BACKGROUND OF THE INVENTION

Drug-eluting implantable medical devices are useful for their ability to provide structural support while medically treating the area in which they are implanted. For example, drug-eluting stents have been used to prevent restenosis in coronary arteries. Drug-eluting stents may administer therapeutic agents such as anti-inflammatory compounds that block local invasion/activation of monocytes, thus preventing the secretion of growth factors that may trigger VSMC proliferation and migration. Other potentially anti-restenotic compounds include antiproliferative agents, such as chemotherapeutics, which include sirolimus and paclitaxel. Other classes of drugs such as anti-thrombotics, anti-oxidants, platelet aggregation inhibitors and cytostatic agents have also been suggested for anti-restenotic use.

Drug-eluting medical devices may be coated with a polymeric material which, in turn, is impregnated with a drug or a combination of drugs. Once the medical device is implanted at a target location, the drug is released from the polymer for treatment of the local tissues. The drug is released by a process of diffusion through a polymer layer of a biostable polymer, and/or as the polymer material degrades when the polymer layer is of a biodegradable polymer.

Drug impregnated polymer coatings are limited in the quantity of the drug to be delivered by the amount of a drug that the polymer coating can carry and the size of the medical device. As well, controlling the rate of elution using polymer coatings is difficult.

Accordingly, drug-eluting medical devices that enable increased quantities of a drug to be delivered by the medical device, and allow for improved control of the elution rate of the drug, and improved methods of forming such medical devices are needed. U.S. Patent Application Publication No. 2011/0008405, filed Jul. 9, 2009, U.S. Provisional Application No. 61/244,049, filed Sep. 20, 2009, U.S. Provisional Application No. 61/244,050, filed Sep. 20, 2009, and co-pending U.S. Patent Application Publication No. 2012/0067008, each incorporated by reference herein in their entirety, disclose methods for forming drug-eluting stents with hollow struts. Polymer-free drug-eluting stents formed with hollow struts can achieve similar elution profiles as drug-eluting stents with the therapeutic substance disposed in a polymer on the surface of the stent. Polymer-free drug-eluting stents formed with hollow struts achieving similar elution profiles as drug-polymer coated stent are expected to have similar clinical efficacy while simultaneously being safer without the polymer coating.

However, it is currently difficult for a physician to customize or tailor the elution profile of a polymer-free drug-eluting stent to meet individual requirements of a specific patient. Accordingly, embodiments hereof relate to methods of and apparatuses to enable a physician to customize or tailor the elution profile of a polymer-free drug-eluting stent.

BRIEF SUMMARY OF THE INVENTION

Embodiments hereof are directed to methods and apparatus for customizing an elution rate or profile of a stent after manufacture of the stent has been completed. The stent is provided after manufacture of the stent has been completed. The stent includes a plurality of side ports for eluting a drug formulation within a lumenal space of a hollow strut that forms the stent. An effective diameter of at least one side port of the plurality of side ports of the stent is modified in order to customize an elution profile of the stent.

In an embodiment hereof, the stent is provided after manufacture of the stent has been completed. The stent includes a plurality of side ports for eluting a drug formulation within a lumenal space of a hollow strut that forms the stent and the plurality of side ports are completely blocked with a filler material during the manufacture of the stent. At least a portion of the filler material is removed from at least one side port of the plurality of side ports to form a channel through the filler material, the channel thereby forming an effective diameter of the at least one side port, to thereby increase the effective diameter of the at least one side port and customize an elution profile of the stent.

In another embodiment hereof, the stent is provided after manufacture of the stent has been completed. The stent includes a plurality of side ports for eluting a drug formulation within a lumenal space of a hollow strut that forms the stent and the plurality of side ports are open following the manufacture of the stent. At least one side port of the plurality of side ports of the stent is at least partially filled with a filler material to form a channel with the filler material, the channel thereby forming an effective diameter of the at least one side port, to thereby decrease the effective diameter of the at least one side port and customize an elution profile of the stent.

In another embodiment hereof, the stent is provided after manufacture of the stent has been completed. The stent includes a plurality of side ports for eluting a drug formulation within a lumenal space of a hollow strut that forms the stent and the lumenal space of the hollow strut is filled to a maximum capacity with the drug formulation during the manufacture of the stent. The stent is soaked within a liquid to remove at least a portion of the drug formulation from the lumenal space of the hollow strut to thereby customize an elution profile of the stent.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Drug eluting stents described herein may be utilized in the context of treatment of blood vessels such as the coronary, carotid and renal arteries, or any other body passageways where it is deemed useful. More particularly, drug eluting stents loaded with a therapeutic substance by methods described herein are adapted for deployment at various treatment sites within the patient, and include vascular stents (e.g., coronary vascular stents and peripheral vascular stents such as cerebral stents), urinary stents (e.g., urethral stents and ureteral stents), biliary stents, tracheal stents, gastrointestinal stents and esophageal stents. In addition, the methods and apparatuses disclosed herein for customizing an elution profile of a stent after manufacture of the stent has been completed may also be utilized for customizing an elution profile of any drug eluting medical device that is configured for implantation within or onto the body, including but not limited to staples, other vascular closure devices, bone screws, or other implants. Furthermore, there is no intention to be bound by any expressed or implied theory presented in the preceding technical field, background, brief summary or the following detailed description.

Hollow Strut Drug-Eluting Stent

Figure 1:
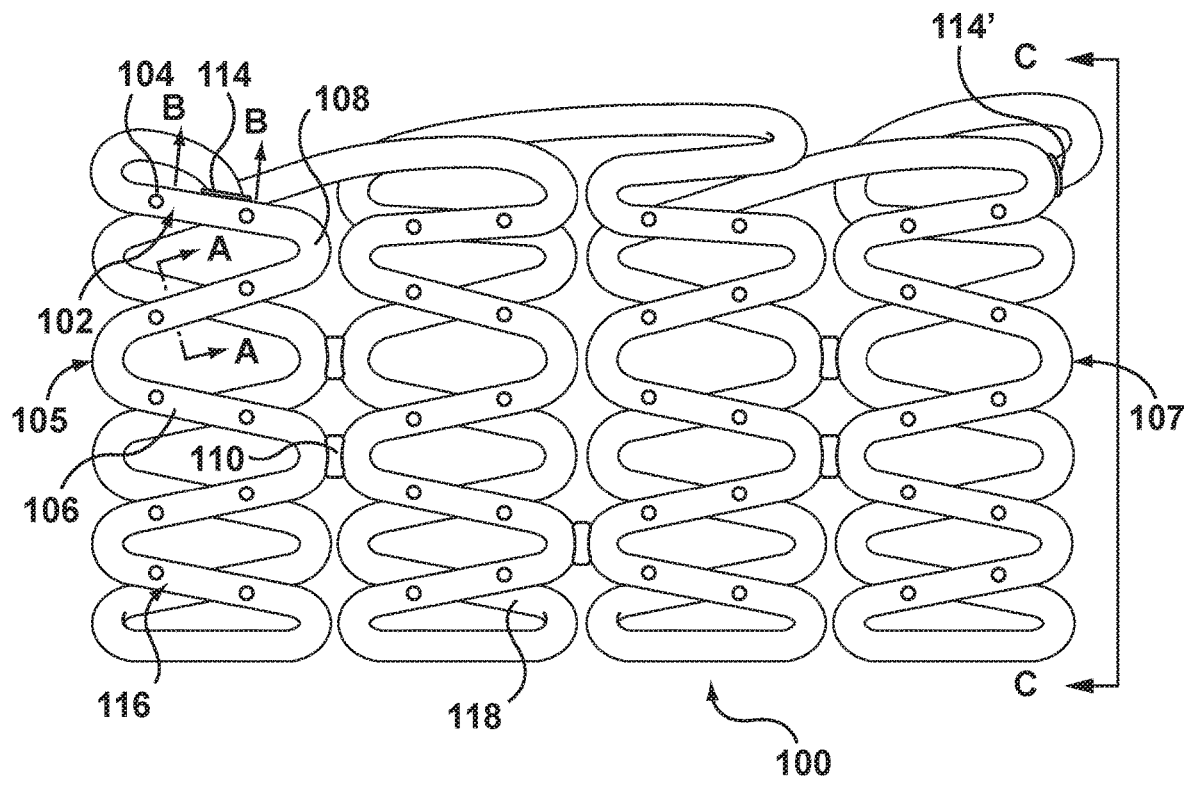
FIG. 1 is a side view of a drug eluting stent formed from a hollow strut according to one embodiment hereof.
Figures 2A, 2B, 2C:
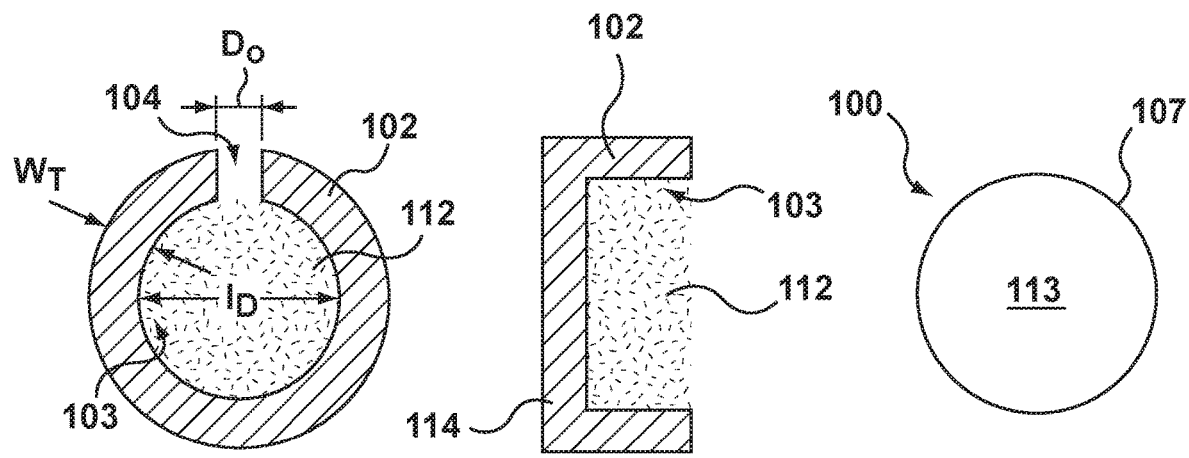
FIG. 2A is a cross-sectional view taken along line A-A of FIG. 1.
FIG. 2B is a sectional view taken along line B-B at an end of the hollow strut of FIG. 1.
FIG. 2C is an end view taken along line C-C of FIG. 1
Figure 3:
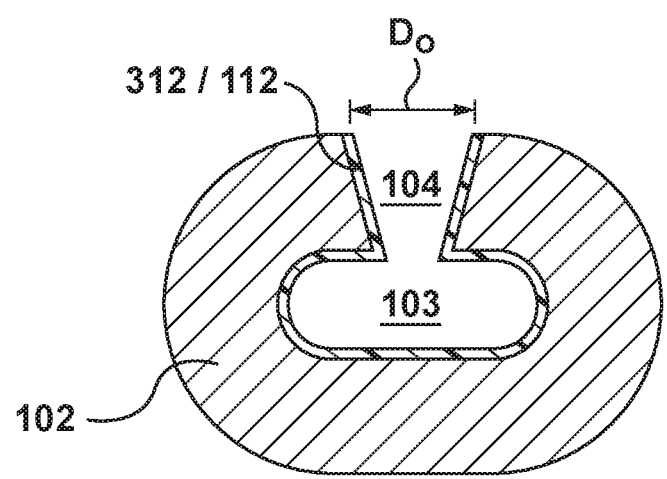
FIG. 3 is a cross-sectional view taken along line A-A of FIG. 1 according to another embodiment hereof.

An embodiment of a stent 100 to be loaded with a drug in accordance with embodiments hereof is shown in FIGS. 1-3. Stent 100 is formed from a hollow strut or wire 102 and hereinafter may be referred to as a stent or a hollow core stent. Hollow strut 102 defines a lumen or lumenal space 103, which may be formed before or after being shaped into a desired stent pattern. In other words, as used herein, "a stent formed from a hollow strut" includes a straight hollow strut shaped into a desired stent pattern or a stent constructed from any suitable manufacturing method that results in a tubular component formed into a desired stent pattern, the tubular component having a lumen or lumenal space extending continuously there-through. As shown in FIG. 1, hollow strut 102 is formed into a series of generally sinusoidal waves including generally straight segments 106 joined by bent segments or crowns 108 to form a waveform that is wound around a mandrel or other forming device to form a generally cylindrical stent 100 that defines a central blood flow passageway or lumen 113 (shown in FIG. 2C) there-through that extends from a first end or tip 105 to a second end or tip 107 of stent 100. Selected crowns 108 of longitudinally adjacent turns of the waveform may be joined by, for example, fusion points or welds 110 as shown in FIG. 1. Methods of filling a drug within a stent in accordance with embodiments hereof are not limited to stents having the pattern shown in FIG. 1. Stent 100 is not limited to the pattern shown in FIG. 1. Hollow strut 102 may be formed into any pattern suitable for use as a stent. For example, and not by way of limitation, hollow strut 102 may formed into stent patterns disclosed in U.S. Pat. No. 4,886,062 to Wiktor, U.S. Pat. No. 5,133,732 to Wiktor, U.S. Pat. No. 5,782,903 to Wiktor, U.S. Pat. No. 6,136,023 to Boyle, and U.S. Pat. No. 5,019,090 to Pinchuk, each of which is incorporated by reference herein in its entirety.

As shown in FIG. 2A, hollow strut 102 of stent 100 allows for a therapeutic substance or drug 112 to be deposited within lumen or lumenal space 103 of hollow strut 102. Although lumenal space 103 is shown as uniformly filled with therapeutic substance or drug 112 in FIG. 2A, therapeutic substance or drug 112 is not required to fill or be uniformly dispersed within the lumenal space 103 of hollow strut 102 but is only required to occupy at least a portion of the lumenal space. Stated another way, in an embodiment hereof, lumenal space 103 may be intentionally or purposely only partially filled. Further, as shown in the embodiment of FIG. 3, therapeutic substance or drug 112 may be disposed within lumenal space 103 as a layer of film or coating 312 on an inner surface of hollow strut 102. When therapeutic substance or drug 112 is disposed within lumenal space 103 as coating 312, blood enters into lumenal space 103 when stent 100 is implanted in situ. When blood comes into contact with coating 312, elution of therapeutic substance or drug 112 is initiated. Lumenal space 103 may continuously extend from a first end 114 to a second end 114' of hollow strut 102. Although hollow strut 102 is shown as generally having a circular cross-section, hollow strut 102 may be generally elliptical or rectangular in cross-section. Hollow strut 102 may have a wall thickness WT in the range of 0.0004 to 0.005 inch with an inner or lumen diameter ID ranging from 0.0005 to 0.02 inch. Hollow strut 102 that forms stent 100 may be made from a metallic material for providing artificial radial support to the wall tissue, including but not limited to stainless steel, nickel-titanium (nitinol), nickel-cobalt alloy such as MP35N, cobalt-chromium, tantalum, titanium, platinum, gold, silver, palladium, iridium, and the like. Alternatively, hollow strut 102 may be made from a hypotube, which is a hollow metal tube of a very small diameter of the type typically used in manufacturing hypodermic needles. Alternatively, hollow strut 102 may be formed from a non-metallic material, such as a polymeric material. The polymeric material may be biodegradable or bioresorbable such that stent 100 is absorbed in the body after being utilized to restore patency to the lumen and/or provide drug delivery.

Hollow strut 102 further includes drug-delivery side openings or ports 104 dispersed along its length to permit therapeutic substance or drug 112 to be released from lumenal space 103. Side ports 104 may be disposed only on generally straight segments 106 of stent 100, only on crowns 108 of stent 100, or on both generally straight segments 106 and crowns 108. Side ports 104 are sized and shaped for a maximum or maximized elution rate of therapeutic substance or drug 112 from stent 100, and as explained in more detail herein, an effective diameter of side ports 104 may be modified after manufacture of stent 100 in order to customize the elution profile of stent 100. Side ports 104 may be, for example and not by way of limitation, 30 μm in width or diameter. Side ports 104 may be slits or may be holes having any suitable cross-section including but not limited to circular, oval, rectangular, or any polygonal cross-section. Side ports 104 may be provided only on an outwardly facing or abluminal surface 116 of stent 100, as shown in FIG. 2, only on the inwardly facing or lumenal surface 118 of stent 100, on both surfaces, or may be provided anywhere along the circumference of hollow strut 102.

In various embodiments hereof, a wide range of therapeutic agents or drugs may be utilized as the elutable therapeutic substance or drug 112 contained in lumenal space 103 of hollow strut 102, with the pharmaceutically effective amount being readily determined by one of ordinary skill in the art and ultimately depending, for example, upon the condition to be treated, the nature of the therapeutic agent itself, the tissue into which the dosage form is introduced, and so forth. Further, it will be understood by one of ordinary skill in the art that one or more therapeutic substances or drugs may be loaded into hollow strut 102. Therapeutic substance or drug 112 delivered to the area of a stenotic lesion can be of the type that dissolves plaque material forming the stenosis or can be an anti-platelet formation drug, an anti-thrombotic drug, or an anti-proliferative drug. Such drugs can include TPA, heparin, urokinase, sirolimus or analogues of sirolimus, for example. Of course stent 100 can be used for delivering any suitable medications to the walls and interior of a body vessel including one or more of the following: anti-thrombotic agents, anti-proliferative agents, anti-inflammatory agents, anti-migratory agents, agents affecting extracellular matrix production and organization, antineoplastic agents, antimitotic agents, anesthetic agents, anti-coagulants, vascular cell growth promoters, vascular cell growth inhibitors, cholesterol-lowering agents, vasodilating agents, and agents that interfere with endogenous vasoactive mechanisms.

In accordance with embodiments hereof, stent 100 is loaded or filled with therapeutic substance or drug 112 prior to implantation into the body. Therapeutic substance or drug 112 is generally mixed with a solvent or dispersion medium/dispersant in order to be loaded into lumenal space 103 of hollow strut 102. In addition, the therapeutic substance or drug 112 can be mixed with an excipient to assist with elution in addition to the solvent or dispersion medium/dispersant in order to be loaded into lumenal space 103 of hollow strut 102. Hereinafter, the term "drug formulation" may be used to refer generally to therapeutic substance or drug 112, a solvent or dispersion medium, and any excipients/additives/modifiers added thereto. In one embodiment, therapeutic substance or drug 112 is mixed with a solvent or solvent mixture as a solution before being loaded into hollow strut 102. A solution is a mixture in which therapeutic substance or drug 112 dissolves within a solvent or a solvent mixture. In one embodiment, a solution includes a high-capacity solvent which is an organic solvent that has a high capacity to dissolve therapeutic substance or drug 112. High capacity as utilized herein is defined as an ability to dissolve therapeutic substance or drug 112 at concentrations greater than 500 mg of substance per milliliter of solvent. Examples of high capacity drug dissolving solvents for sirolimus and similar substances include but are not limited to tetrahydrofuran (THF), di-chloromethane (DCM), chloroform, and di-methyl-sulfoxide (DMSO). In addition to the high-capacity solvent, a solution may include an excipient to assist in drug elution. In one embodiment, an excipient may be a surfactant such as but not limited to sorbitan fatty acid esters such as sorbitan monooleate and sorbitan monolaurate, polysorbates such as polysorbate 20, polysorbate 60, and polysorbate 80, cyclodextrins such as 2-hydroxypropyl-beta-cyclodextrin and 2,6-di-O-methyl-beta-cyclodextrin, sodium dodecyl sulfate, octyl glucoside, and low molecular weight poly(ethylene glycol)s. In another embodiment, an excipient may be a hydrophilic agent such as but not limited to salts such as sodium chloride and other materials such as urea, citric acid, and ascorbic acid. In yet another embodiment, an excipient may be a stabilizer such as but not limited to butylated hydroxytoluene (BHT). Depending on the desired drug load, a low capacity solvent can also be chosen for its decreased solubility of therapeutic substance or drug 112. Low capacity is defined as an ability to dissolve therapeutic substance or drug 112 at concentrations typically below 500 mg of drug per milliliter solvent. Examples of low capacity drug dissolving solvents for sirolimus and similar substances include but are not limited to methanol, ethanol, propanol, acetonitrile, ethyl lactate, acetone, and solvent mixtures like tetrahydrofuran/water (9:1 weight ratio). After a solution is loaded into stent 100, therapeutic substance or drug 112 may be precipitated out of the solution, e.g., transformed into solid phase, and the majority of the residual solvent and any nonsolvent, if present, may be extracted from the lumenal space of hollow strut 102 such that primarily only therapeutic substance or drug 112 or therapeutic substance or drug 112 and one or more excipients remain to be eluted into the body.

In another embodiment, therapeutic substance or drug 112 is mixed with a dispersion medium as a slurry/suspension before being loaded into hollow strut 102. In a slurry/suspension form, therapeutic substance or drug 112 is not dissolved but rather dispersed as solid particulate in a dispersion medium, which refers to a continuous medium in liquid form within which the solid particles are dispersed. Examples of dispersion mediums with an inability to dissolve therapeutic substance or drug 112 depend on the properties of therapeutic substance or drug 112. For example, suitable dispersion mediums with an inability to dissolve sirolimus include but are not limited to water, hexane, and other simple alkanes, e.g., C5 thru C10. Certain excipients, suspending agents, surfactants, and/or other additives/modifiers can be added to the drug slurry/suspension to aid in suspension and stabilization, ensure an even dispersion of drug throughout the suspension and/or increase the surface lubricity of the drug particles. Surfactants thus generally prevent therapeutic substance or drug 112 from floating on the top of or sinking to the bottom of the dispersion medium and also prevent particles of therapeutic substance of therapeutic substance or drug 112 from clumping. Examples of surfactants include but are not limited to sorbitan fatty acid esters such as sorbitan monooleate and sorbitan monolaurate, polysorbates such as polysorbate 20, polysorbate 60, and polysorbate 80, and cyclodextrins such as 2-hydroxypropyl-beta-cyclodextrin and 2,6-di-O-methyl-beta-cyclodextrin. In one embodiment, the targeted amount of therapeutic substance or drug 112 is suspended in the dispersion medium and the appropriate additive/modifier is added on a 0.001 to 10 wt % basis of total formulation. In addition, an excipient such as urea or 2,6-di-O-methyl-beta-cylcodextrin may be added to the slurry/suspension to assist in drug elution.

Open ends 114, 114' of hollow strut 102 may be closed or sealed either before or after the drug is loaded within lumenal space 103 as shown in the sectional view of FIG. 2B, which is taken along line 2B-2B of FIG. 1. Once positioned inside of the body at the desired location, stent 100 is deployed for permanent or temporary implantation in the body lumen such that therapeutic substance or drug 112 may elute from lumenal space 103 via side ports 104.

Stent 100 has a radially compressed configuration sufficient for delivery to the treatment site within a catheter-based delivery system or other minimally invasive delivery system and a radially expanded or deployed configuration in which stent 100 comes into contact with the vessel. In an embodiment hereof, stent 100 is balloon-expandable. Stent 100 is collapsed or crimped to the radially compressed or unexpanded configuration around the balloon of a balloon catheter for delivery to a treatment site, such as the type of balloon used in an angioplasty procedure. As the balloon expands, it physically forces stent 100 to radially expand such that the outside surface of stent 100 comes into contact with the lumen wall. The balloon is then collapsed leaving stent 100 in the radially expanded or deployed configuration. Conventional balloon catheters that may be used in the present invention include any type of catheter known in the art, including over-the-wire catheters, rapid-exchange catheters, core wire catheters, and any other appropriate balloon catheters. For example, conventional balloon catheters such as those shown or described in U.S. Pat. Nos. 6,736,827, 6,554,795, 6,500,147, and 5,458,639, which are incorporated by reference herein in their entirety, may be used as the delivery system for stent 100.

In another embodiment hereof, stent 100 may be self-expanding. The term "self-expanding" is used in the following description is intended to convey that the structures are shaped or formed from a material that can be provided with a mechanical memory to return the structure from a compressed or constricted delivery configuration to an expanded deployed configuration. Non-exhaustive exemplary self-expanding materials include stainless steel, a pseudo-elastic metal such as a nickel titanium alloy or nitinol, various polymers, or a so-called super alloy, which may have a base metal of nickel, cobalt, chromium, or other metal. Mechanical memory may be imparted to a wire or stent structure by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well, poly L-D lactic copolymer, oligo caprylactone copolymer and poly cyclo-octine can be used separately or in conjunction with other shape memory polymers.

Customizing the Elution Profile of Stent 100

Embodiments hereof relate to customizing or tailoring the elution rate or profile of stent 100 after the manufacture thereof to meet individual requirements of a specific patient. The elution profile determines how quickly or slowly the drug will elute from the stent in vivo. During manufacture, an original diameter $D_O$ (shown on FIG. 2A and FIG. 3) of side ports 104 is sized or configured for a maximum or maximized elution rate of therapeutic substance or drug 112 from stent 100. The original diameter $D_O$ of side ports 104 may be modified after manufacture of stent 100 has been completed in order to customize the elution profile of stent 100. Stated another way, the elution profile of a standard or an off-the-shelf product may be modified by a physician in order to meet individual requirements of a specific patient. For example, diabetic patients or patients with an upcoming surgery require a relatively fast and/or short elution profile while high risk patients require a relatively slow and/or long elution profile. By way of example only, the elution profile of stent 100 may be modified by a physician in a catheterization laboratory or cath lab, which is an examination room in a hospital or clinic with diagnostic imaging equipment used to visualize the arteries of the heart and the chambers of the heart and treat any stenosis or abnormality found. More particularly, as will be described in more detail herein, the number (quantity) and/or size (diameter) of side ports 104 can be modified in the cath lab by the physician in order to vary the quantity and/or rate of therapeutic substance or drug 112 being eluted out of side ports 104 and thereby customize the elution profile of stent 100. As used herein, diameter is a transverse measurement of a particular element or component, such as but not limited to hollow strut 102 and side port 104, and the particular element is not required to be circular or spherical in shape. The elution profile or rate of stent 100 is determined by the precise pattern of side ports 104 (i.e., which side ports 104 are open and which side ports 104 are plugged as will be described in more detail herein), as well as the dimension of the effective diameter (which is described in more detail herein) of each side port 104 that is open.

Figure 4:
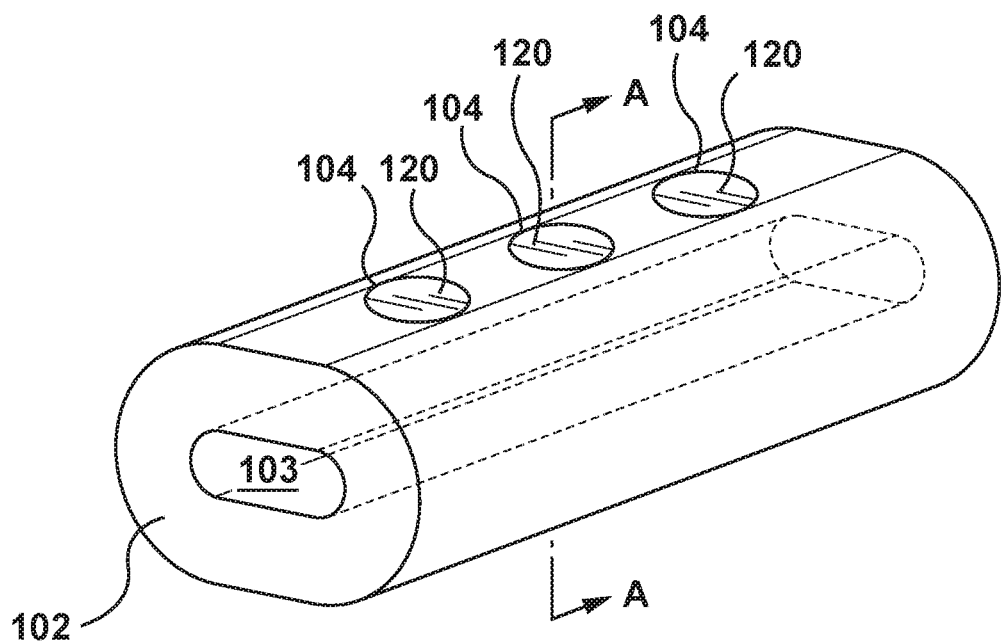
FIG. 4 is a perspective view of a portion of the drug eluting stent of FIG. 1 according to an embodiment hereof, wherein the drug eluting stent includes a plurality of elution openings that are filled with a filler material during manufacture of the stent.
Figure 4A:
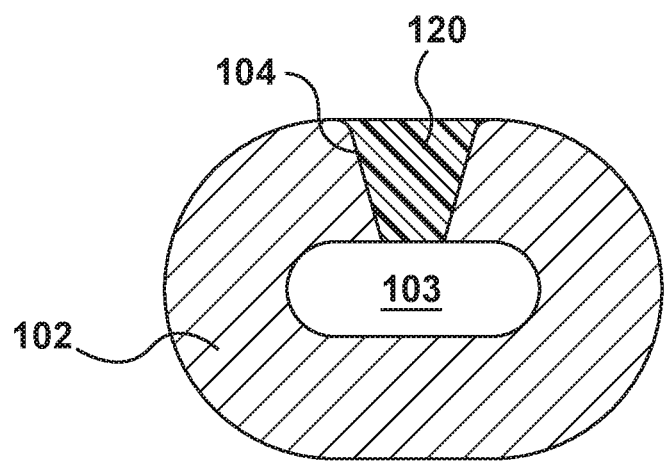
FIG. 4A is a cross-sectional view taken along line A-A of FIG. 4.

In an embodiment hereof, all side ports 104 are completely blocked or plugged with a sacrificial filler material during the manufacture of stent 100 and at least a portion of the filler material is removed to increase an effective diameter of at least one side port 104 to customize an elution profile of 100 stent. The filler material may be considered sacrificial in that at least a portion thereof is removed during such customization and prior to use of stent 100. More particularly, as shown in FIGS. 4 and 4A, side ports 104 are filled with a filler material 120 during manufacture of stent 100, stent 100 is loaded onto a catheter, and shipped to the customer. FIG. 4 is a perspective view of a portion of stent 100 illustrating side ports 104 blocked or plugged with filler material 120, and FIG. 4A is a cross-sectional view taken along line A-A of FIG. 4. Filler material 120 completely or fully blocks side ports 104 such that filler material 120 is essentially a plug for each respective side port 104. In an embodiment, filler material 120 is a bioabsorbable or biodegradable polymer such as but not limited to polylactic acid (PLLA), polycaprolactone, and aliphatic polyesters. In another embodiment, filler material 120 is magnesium. In another embodiment, filler material 120 is a biostable material such as but not limited to polyethylene, polyurethane, and polypropylene.

Figure 5:
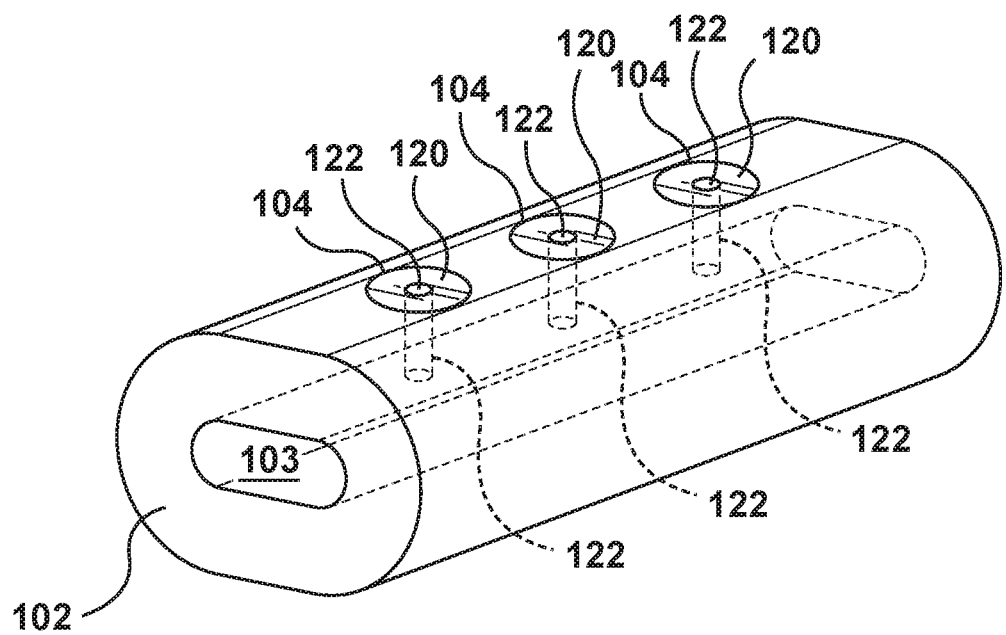
FIG. 5 is a perspective view of the portion of the drug eluting stent of FIG. 4, wherein at least a portion of the filler material has been removed each of the plurality of side ports.
Figure 5A:
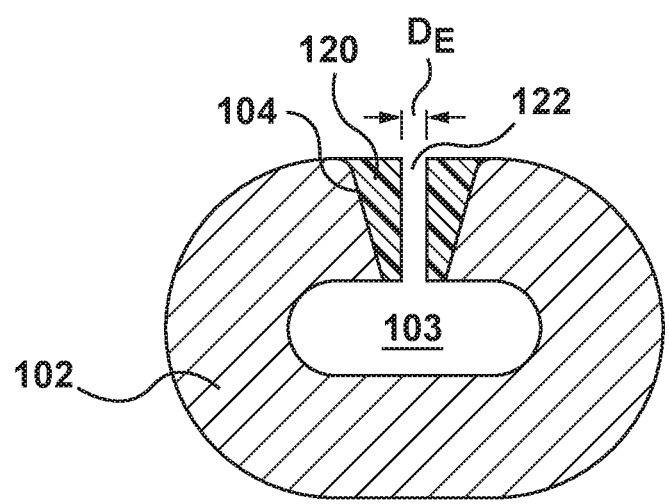
FIG. 5A is a cross-sectional view taken along line A-A of FIG. 5.

At least a portion of filler material 120 is removed from at least one side port 104 of the plurality of side ports to form a channel 122 through filler material 120 as shown in FIGS. 5 and 5A. FIG. 5 is a perspective view of a portion of stent 100 illustrating side ports 104 after removal of a portion of filler material 120 from each side port 104, and FIG. 5A is a cross-sectional view taken along line A-A of FIG. 5. Each channel 122 extends through the thickness of filler material 120 such that each channel 122 is in fluid communication with lumenal space 103 of hollow strut 102 to permit elution of therapeutic substance or drug 112 from lumenal space 103 through channel 122 formed within side port 104. Each channel 122 forms an effective diameter $D_E$ of its respective side port 104. "Effective diameter" as used herein refers to the diameter of side port 104 with filler material 120 therein after customization of the side port has been performed by the physician. Stated another way, the diameter of each channel 122 is the effective diameter of side port 104 because elution of therapeutic substance or drug 112 occurs through channel 122 formed within side port 104. If all filler material 120 is removed from a respective side port 104, the effective diameter $D_E$ of the side port 104 is equal to the original diameter $D_O$ of the side port 104. Relative to the state of FIGS. 4 and 4A in which filler material 120 completely or fully blocks side port 104, removal of at least a portion of filler material 120 thereby increases the effective diameter $D_E$ of the respective side port 104 and customizes an elution profile of the stent. The elution rate of stent 100 is controlled by effective diameters $D_E$ of side ports 104 which can be controlled by removing a predetermined or select amount of filler material 120. The amount of filler material 120 removed from each side port 104 may be tailored to the patient requirements. As will be described in more detail herein, the use of an agent (such as but not limited to a reagent or etching gas), light, mechanical force, or heat may be used to selectively remove filler material 120 to open side ports 104 to varying degrees to create a customizable drug elution profile.

Figure 6A:
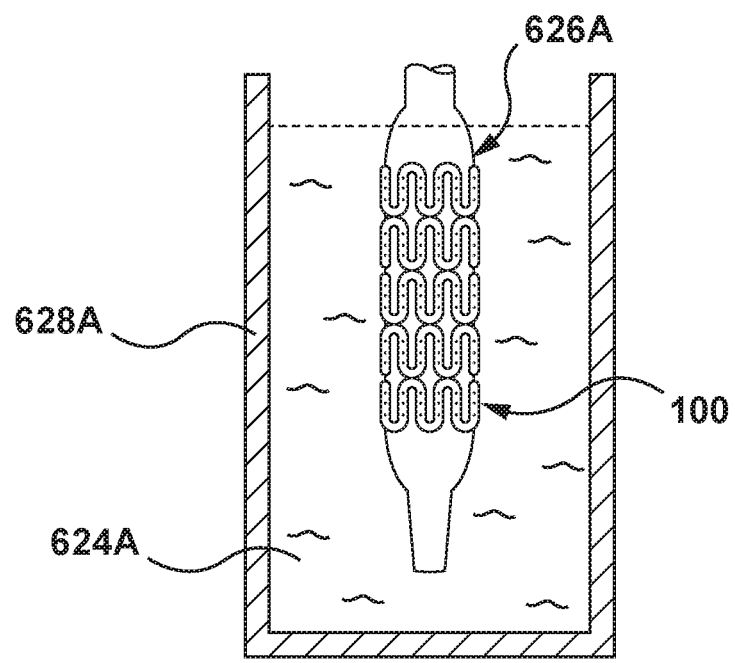
FIG. 6A illustrates a method of removing at least a portion of the filler material from each of the plurality of side ports according to an embodiment hereof, wherein the method includes a submersing the drug eluting stent into a bath of a liquid reagent.
Figure 7:
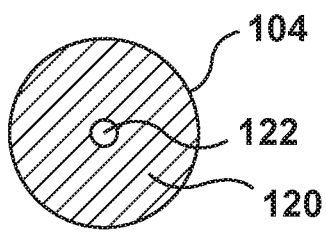
FIG. 7 is a top view of an elution hole after removal of the filler material following a first predetermined elapsed time period.
Figure 8:
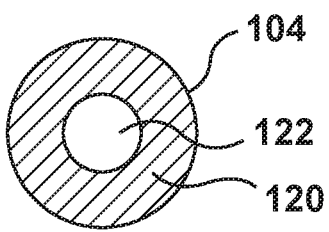
FIG. 8 is a top view of an elution hole after removal of the filler material following a second predetermined elapsed time period.
Figure 9:
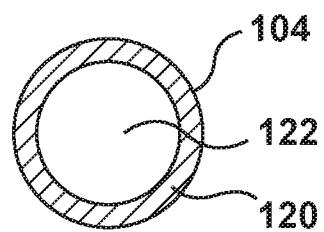
FIG. 9 is a top view of an elution hole after removal of the filler material following a third predetermined elapsed time period.

In one embodiment, removing filler material 120 is achieved by exposing filler material 120 to a reagent for a predetermined amount of time in order to chemically dissolve, erode, or otherwise remove a portion of filler material 120. In an embodiment, the reagent is an acid or other liquid reagent such as but not limited to acetone and methyl ethyl ketone (MEK) configured to dissolve or erode filler material 120. For example, as shown in FIG. 6A, stent 100 disposed on a balloon catheter 626A is lowered into an open-ended container 628A such that stent 100 is fully or partially submersed into a bath or reservoir of liquid reagent 624A which would dissolve or erode filler material 120 by a time-dependent amount. It will be apparent to one of ordinary skill in the art that the degree of submersion may vary according to the application and whether all or only a portion of side ports 104 are to be opened via removal of filler material 120. If stent 100 is self-expanding (and thus not pre-loaded onto a balloon catheter), the stent may be lowered into open-ended container 628A via suitable stent suspension means (not shown). After being fully or partially submersed into a bath or reservoir of liquid reagent 624A, the amount of filler material 120 which is dissolved or eroded by liquid reagent 624A varies depending on the length of time that stent 100 is fully or partially submersed within liquid reagent 624A. In addition, the amount of filler material 120 which is dissolved or eroded by liquid reagent 624A varies depending on the type of reagent utilized. Stated another way, different exposure times and/or different reagents (or different reagent concentrations) used controls the amount of filler material 120 removed. FIGS. 7-9 illustrate top views of a side port 104 after removal of at least a portion of filler material 120 following various predetermined elapsed time periods. In FIG. 7, only a small amount of filler material 120 has been removed following a first predetermined elapsed time period. In FIG. 8, following a second predetermined elapsed time period which is longer than the first predetermined elapsed time period, a greater amount of filler material 120 has been removed and thus results in a relatively larger channel 122. In general, larger sized channels 122 generally permit a faster elution rate and smaller sized channels 122 generally provide a slower elution rate. Smaller sized channels 122 generally provide a slower elution rate because filler material 120 prevents or slows the rate at which therapeutic drug 120 egresses or elutes from channels 122/side ports 104. In FIG. 9, almost all of filler material 120 has been eroded or dissolved by liquid reagent 624A following a third predetermined elapsed time period to results in an even relatively larger channel 122. Although not shown, in an embodiment, a physician may choose to remove all of filler material 120 such that side port 104 has its original diameter $D_O$ and a maximum or maximized elution rate.

In another embodiment, the reagent is an etching agent such as but not limited to hydrofluoric acid, phosphoric acid or a chrome etching agent configured to dissolve or erode filler material 120. For example, as shown in FIG. 6B, stent 100 disposed on a balloon catheter 626B is lowered into a sealed or closed container 628B such that stent 100 is fully or partially submersed into a reservoir of etching agent 624B which would dissolve or erode filler material 120 by a time-dependent amount similar to liquid reagent 624A described above.

Figure 6B:
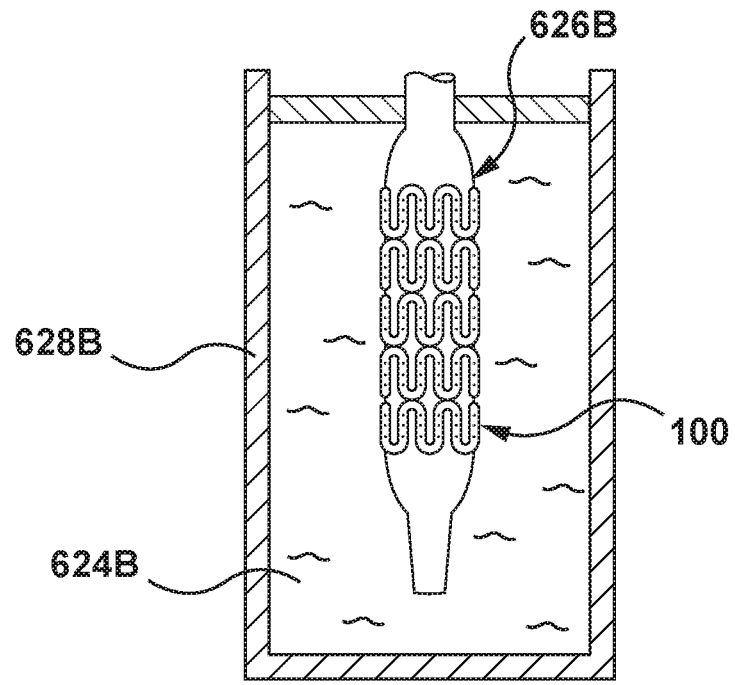
FIG. 6B illustrates a method of removing at least a portion of the filler material from each of the plurality of side ports according to another embodiment hereof, wherein the method includes inserting the drug eluting stent into a container of etching gas.
Figure 10:
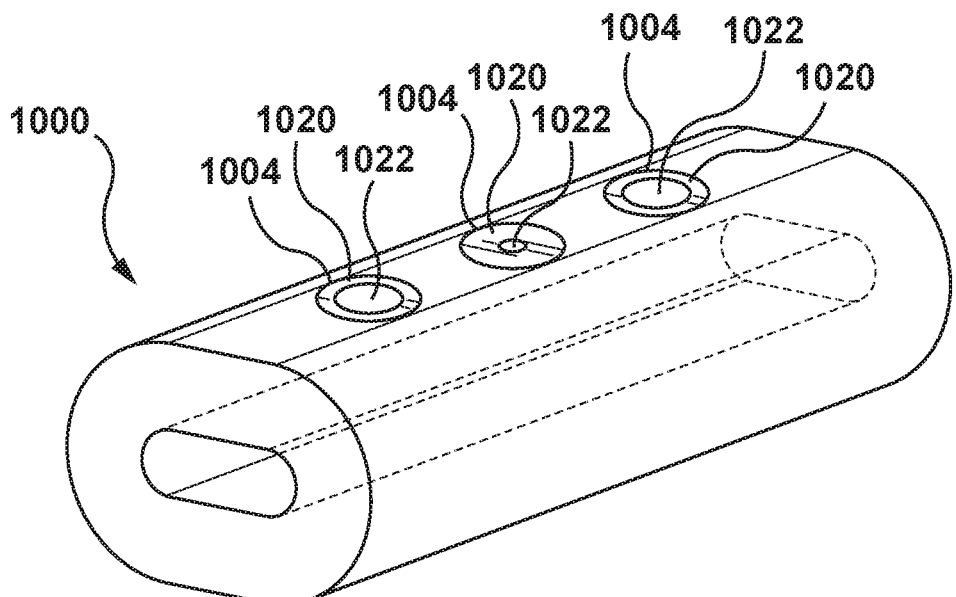
FIG. 10 is a perspective view of the portion of the drug eluting stent of FIG. 4, wherein at least a portion of the filler material has been removed each of the plurality of side ports and the amount of removed filler material varies within the plurality of side ports.
Figure 11:
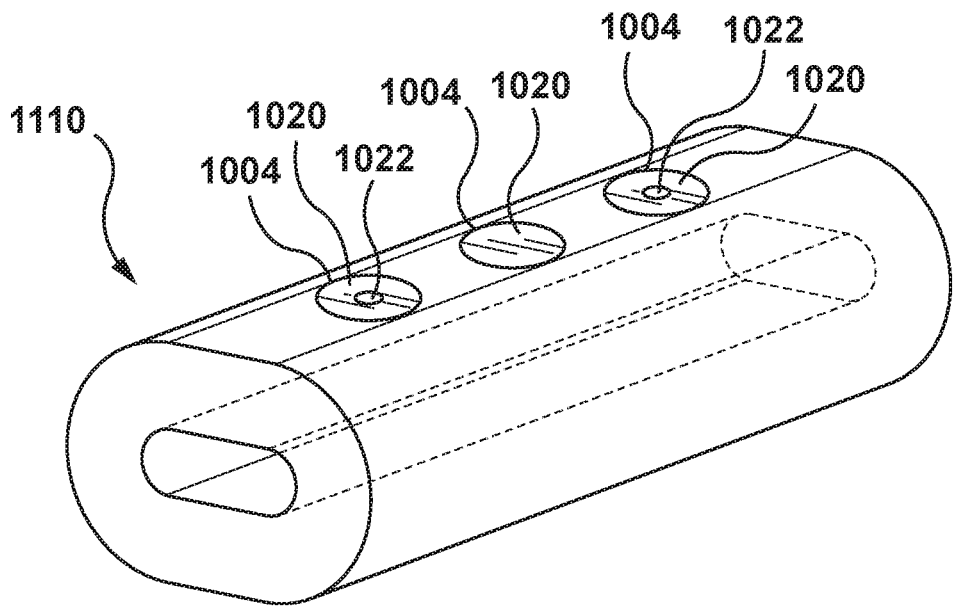
FIG. 11 is a perspective view of the portion of the drug eluting stent of FIG. 4, wherein the filler material has not been removed from each of the plurality of side ports.

In the embodiments of FIGS. 6A and 6B, stent 100 is fully or partially submersed into the liquid reagent or etching gas such that the same amount of filler material 120 is removed from each side port 104 and thus each side port 104 is opened by the same amount as shown in the embodiment of FIG. 5. This is desirable when a consistent elution profile along the entire stent length is required. However, in another embodiment, the quantity of side ports 104 and/or the relative size of channels 122 may be varied along stent 100 in order to vary the quantity and/or rate of therapeutic substance or drug 112 being eluted side ports 104 and thereby customize the elution profile of stent 100. For example, FIG. 10 illustrates a perspective view of a portion of a stent 1000 in which at least a portion of filler material 1020 has been removed from each of the plurality of side ports 1004 but the amount of removed filler material varies along the length of stent 1000. As such, channels 1022 have different diameters and thus side ports 1004 have different effective diameters $D_E$. Removing different amounts of filler material 1020 may be accomplished by manually applying a liquid reagent via a sponge, spray, brush, or another suitable utensil. In the embodiment of FIG. 11, a portion of a stent 1100 is shown in which at least a portion of filler material 1120 has been removed from some of the plurality of side ports 1104 but at least one side port 1104 remains plugged or blocked by filler material 1120. Thus, in this embodiment, only specific side ports 1104 are exposed to a reagent and the filler material 120 is not been removed from at least one side port 1104 of the plurality of side ports of stent 1100.

Figure 12:
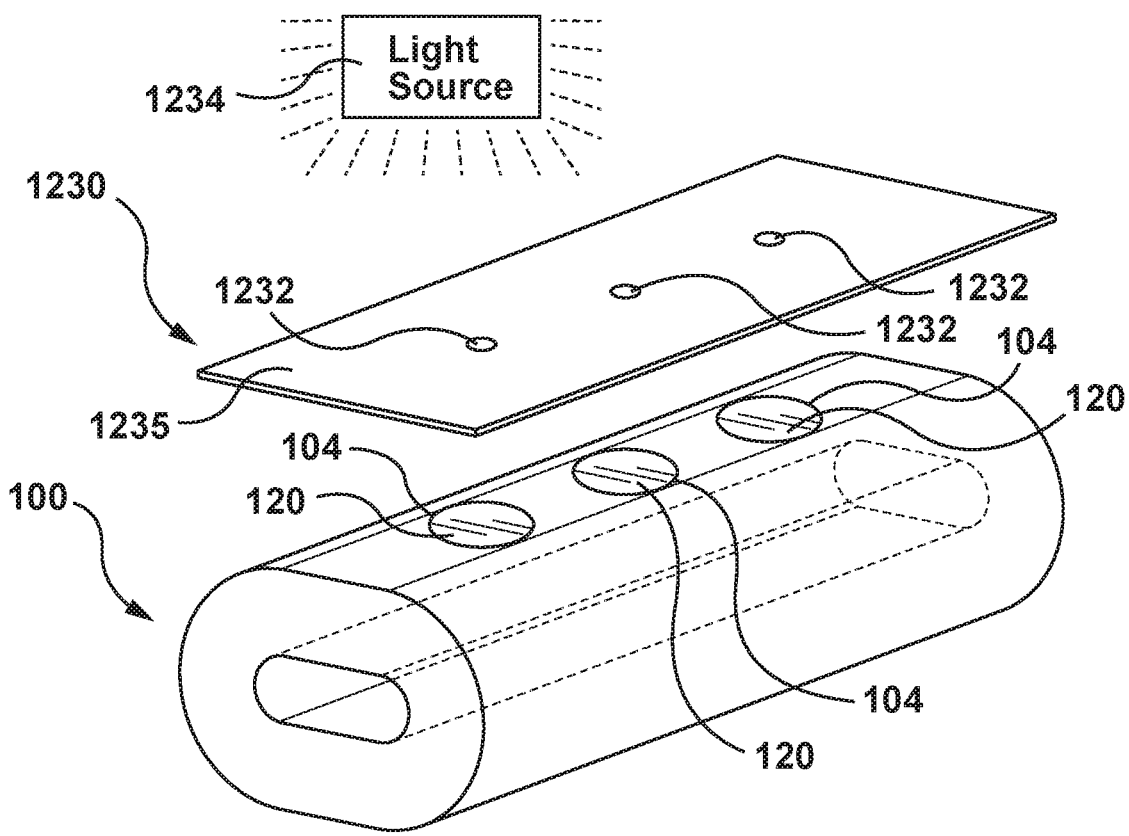
FIG. 12 illustrates a method of removing at least a portion of the filler material from each of the plurality of side ports according to another embodiment hereof, wherein the method includes positioning a stencil over the plurality of side ports and subjecting the filler material to a light source.

In another embodiment, removing filler material 120 is achieved by exposing filler material 120 to at least one light source for a predetermined amount of time in order to dissolve, erode, or otherwise remove a portion of filler material 120. The light source is an ultraviolet or visible light source which has an intensity and/or wavelength configured to dissolve or erode filler material 120. In an embodiment, the light source is a laser. For example, FIG. 12 illustrates a method of removing at least a portion of filler material 120 from each of the plurality of side ports 104 with a light source 1234. A stencil 1230 is positioned over the plurality of side ports 104. Stencil 1230 has a planar or flat body 1235 and a plurality of holes 1232 formed through body 1235. The pattern and size of holes 1232 of stencil 1230 determines the pattern and size of channels 122 to be formed through filler material 120 disposed within side ports 104. The size of channel 122 (and thus the effective diameter $D_E$ of side port 104) will be equal to the size of the respective hole 1232 which is placed over filler material 120. For example, if a consistent elution profile along the entire stent length is required as described above with respect to FIG. 5 and the same amount of filler material 120 is to be removed from each side port 104, holes 1232 of stencil 1230 are all the same size and are spaced to correspond with the pattern of side ports 104. Alternatively, if the quantity of side ports 104 and/or the relative size of channels 122 are required to vary along stent 100 as described above with respect to FIGS. 10 and 11, holes 1232 of stencil 1230 may be formed from different sizes and are spaced to correspond with only side ports 104 which are to have filler material 120 removed. Removing filler material 120 is achieved by positioning holes 1232 of stencil 1230 over the target side ports 104 and then exposing filler material 120 to light from light source 1234 for a predetermined amount of time. Light from light source 1234 has a intensity and a wavelength configured to chemically break down filler material 120 when filler material 120 is exposed to the light for a predetermined amount of time. Only filler material 120 which is exposed to the light breaks down and is removed, such that any filler material 120 which is covered by stencil 1230 does not break down.

Figure 13:
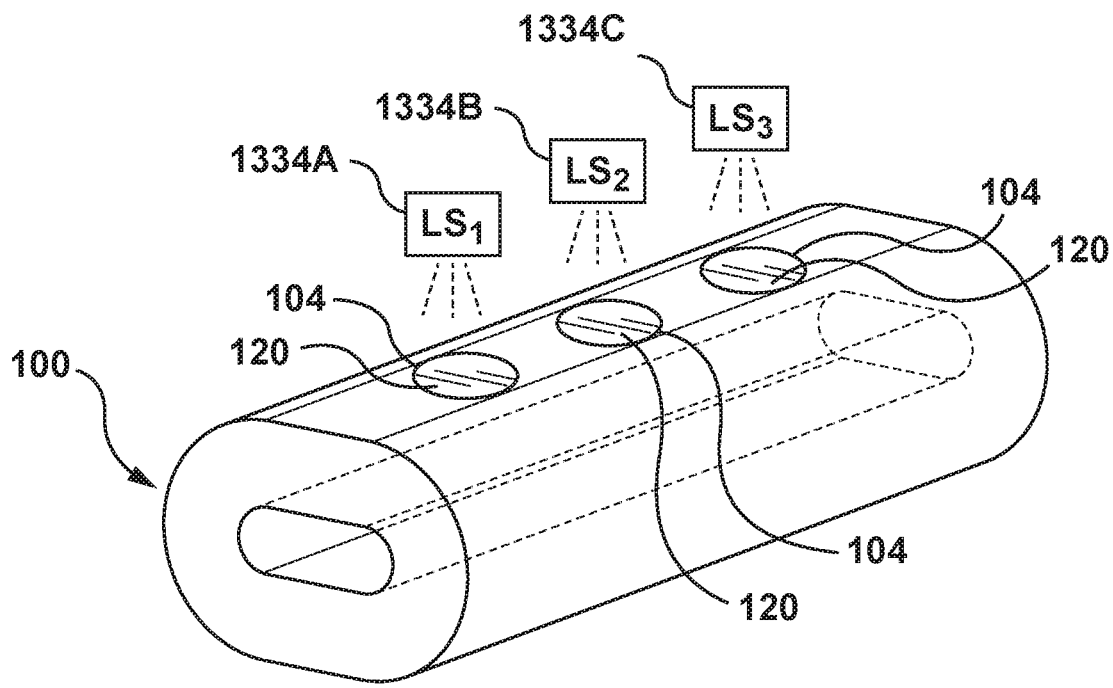
FIG. 13 illustrates a method of removing at least a portion of the filler material from each of the plurality of side ports according to another embodiment hereof, wherein the method includes subjecting the filler material to multiple light sources of differing wavelengths or intensities.

In another embodiment, use of stencil 1230 may be omitted by using various light sources of differing wavelengths and/or intensities. For example, as shown in FIG. 13, a plurality of light sources 1334A, 1334B, and 1334C are positioned such that they each correspond to a single side port 104. Each light source 1334A, 1334B, and 1334C has an intensity and/or wavelength configured to dissolve or erode filler material 120. However, at least one of the light sources are configured to dissolve or erode filler material at a different rate from another of the light sources in order to vary the amount of filler material 120 that is removed from the respective side ports when stent 100 is exposed to light sources 1334A, 1334B, and 1334C for a predetermined amount of time. For example, in order to achieve a side port pattern similar to that shown in FIG. 10, second light source (LS$_2$) 1334B is configured to dissolve or erode filler material slower than first light source (LS$_1$) 1334A and third light source (LS$_3$) 1334C. As such, less filler material 120 is removed from the side port 104 that is exposed to light from second light source 1334B than filler material 120 that is removed from the side ports 104 that are exposed to light from first and third light sources 1334A, 1334C when all side ports 104 are exposed to the light sources for the same predetermined amount of time.

Although FIGS. 12-13 are described with various light sources utilized to remove filler material 120, in another embodiment removing filler material 120 is achieved by exposing filler material 120 to heat for a predetermined amount of time to melt the filler material. Controlled heat from a heat source (not shown) can be used to melt or disrupt filler material 120, which may be for example magnesium as described above. The heat source may be used with a stencil similar to stencil 1230 such that the pattern and size of the holes of the stencil determines the pattern and size of channels 122 to be formed through filler material 120 disposed within side ports 104. Removing filler material 120 is achieved by positioning the holes of the stencil over the target side ports 104 and then exposing filler material 120 to heat from the heat source for a predetermined amount of time. Heat from the heat source has a predetermined intensity to melt filler material 120 when filler material 120 is exposed to the heat for a predetermined amount of time. Only filler material 120 which is exposed to the heat melts and is removed, such that any filler material 120 which is covered by the stencil does not melt. In another embodiment, use of the stencil may be omitted by using various heat sources of differing intensities to target select side ports 104.

Figure 14:
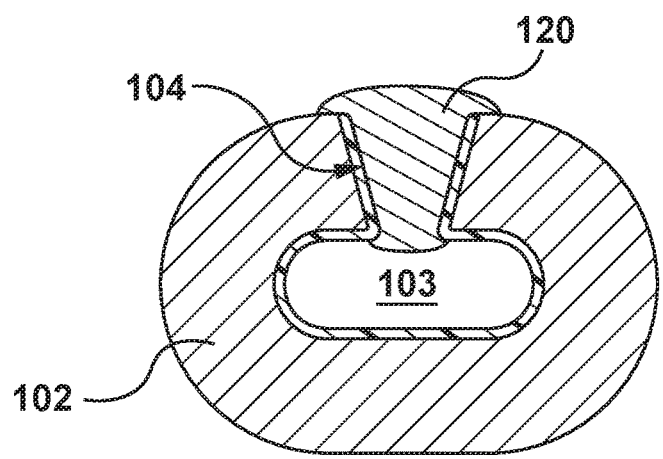
FIG. 14 is a cross-sectional view taken along line A-A of FIG. 4 according to an alternative embodiment hereof.
Figure 15:
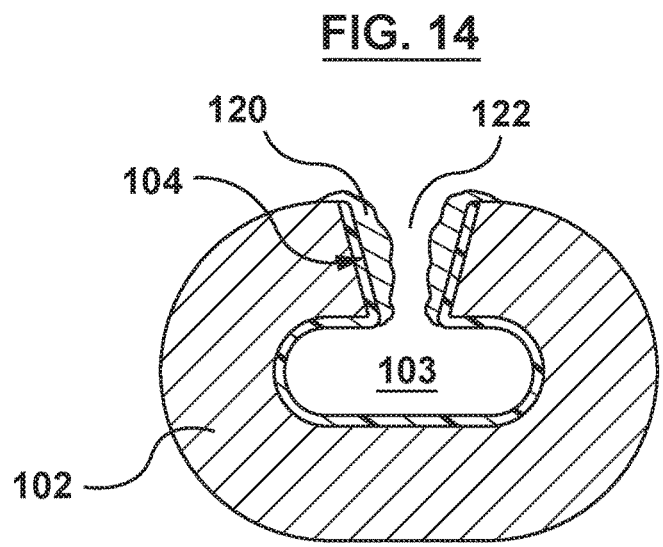
FIG. 15 is the cross-sectional view of FIG. 14 after removal of at least a portion of the filler material following rolling the drug eluting stent for a first predetermined time period.
Figure 16:
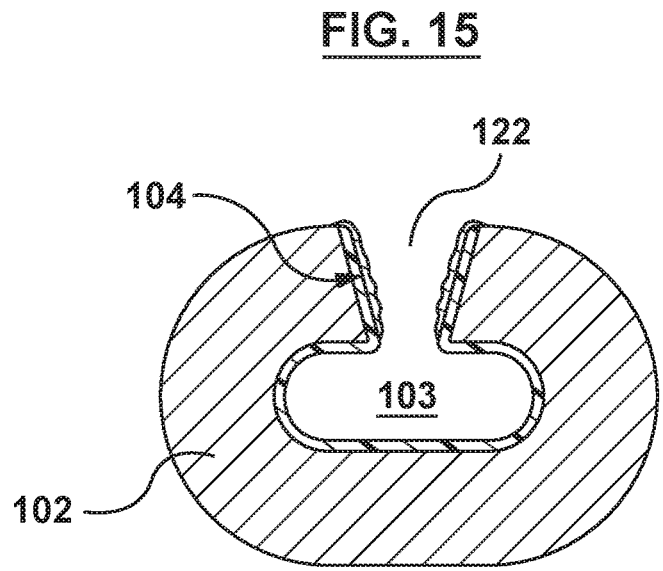
FIG. 16 is the cross-sectional view of FIG. 14 after removal of at least a portion of the filler material following rolling the drug eluting stent for an additional second predetermined time period.

In another embodiment, removing filler material 120 is achieved by mechanically breaking up filler material 120 in order to remove a portion of filler material 120. The physician can choose to roll stent 100 against a hard surface to break up filler material 120, increase the effective diameter D$_E$ of side ports 104, and thereby tailor the elution profile of stent 100. For example, FIGS. 14-16 illustrate cross-sectional views of a side port 104 after removal of filler material 120 following various predetermined elapsed time periods. In FIG. 14, no filler material 120 has been removed and filler material 114 is still disposed within side port 104. In FIG. 15, following a first predetermined time period in which stent 100 is rolled over a hard surface, a portion of filler material 120 has been removed and channel 122 is formed. In FIG. 16, almost all of filler material 120 has been removed following an additional second predetermined time period in which stent 100 is continued to be rolled over a hard surface. As shown, with more filler material 120 removed by the longer period of rolling, channel 122 is larger in size and thus the elution rate therefrom is faster. In general, larger sized channels 122 generally permit a faster elution rate and smaller sized channels 122 generally provide a slower elution rate because filler material 120 prevents or slows the rate at which therapeutic drug 120 egresses or elutes from channels 122/side ports 104.

Figure 17A:
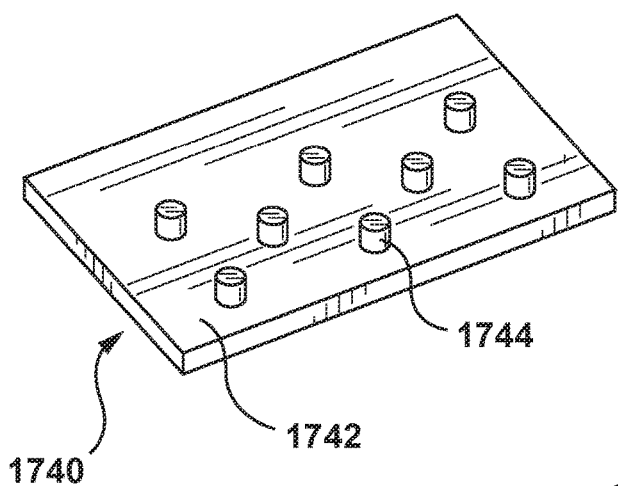
FIG. 17A is a perspective view of a peg board that may be utilized during rolling of the drug eluting stent according to another embodiment hereof, wherein the pegs are configured to mechanically break up filler material within side ports.

In an embodiment, a peg board may be used to control or aid in mechanically breaking up filler material 120 by rolling stent 100. For example, as shown in FIG. 17A, a peg board 1740 includes a planar or flat body 1742 and a plurality of pegs 1744 extending from body 1742. Although shown as generally cylindrical elements, pegs 1744 may have other sizes and/or shapes and such sizes and/or shapes of pegs 1744 may be configured to mechanically break up a predetermined amount of filler material 120. Filler material 120 that covers the top of side port 104 (see FIG. 14) is configured to be positioned over or sit onto a peg 1744 of peg board 1740. In an embodiment, when stent 100 is rolled over peg board 1740, pegs 1744 operate to mechanically break up filler material 120 due to contact between pegs 1744 and filler material 120. As shown on FIGS. 14-16, the longer that stent 100 is rolled over peg board 1740, larger amounts of filler material 120 is broken up to effectively open side port 104. Further, pegs 1744 may be configured to remove a specific or predetermined amount of filler material 120 when stent 100 is rolled over peg board 1740. More particularly, the pattern and/or size (width or diameter) of pegs 1744 of peg board 1740 determines the pattern and size of channels 122 to be formed through filler material 120 disposed within side ports 104. For example, pegs 1744 may be positioned at particular locations on flat body 1742 in order to target removal of filler material 120 from predetermined side ports 104. As another example, pegs 1744 may have different sizes and/or shapes in order to target removal of a predetermined amount of filler material 120 from side ports 104. In general, larger and/or longer pegs may be configured to mechanically break up a larger amount of filler material 120 than smaller and/or shorter pegs given an equal number of rollings. Multiple peg boards may be provided that each provide different desired elution profiles, i.e., rolling stent 100 on a first peg board will remove a certain amount of filler material 120 from a predetermined pattern of side ports 104 in order to customize stent 100 to a short elution profile while rolling stent 100 on a second peg board will remove a certain amount of filler material 120 from a predetermined pattern of side ports 104 in order to customize stent 100 to a longer elution profile.

Figure 17B:
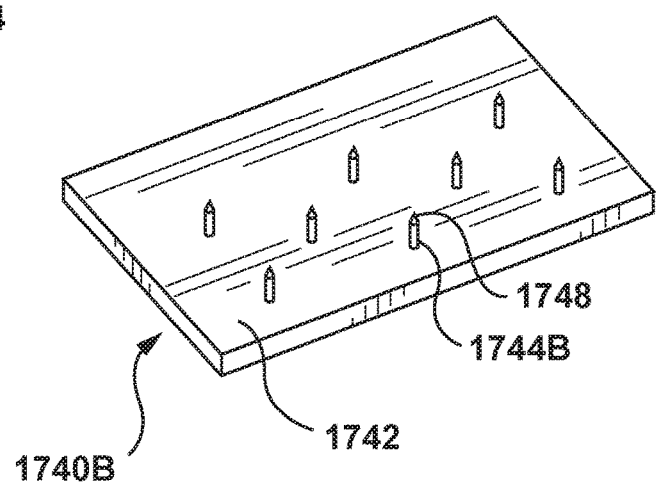
FIG. 17B is a perspective view of a peg board according to another embodiment hereof, wherein the pegs of the peg board are needle-like and are configured to pull out the entire amount of filler material from side ports.
Figure 17C:
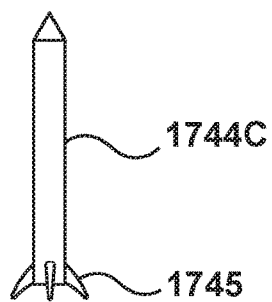
FIG. 17C is a side view of a needle-like peg according to another embodiment hereof, wherein the needle-like peg includes barbs.
Figure 17D:
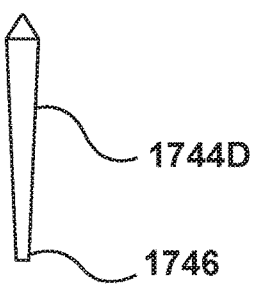
FIG. 17D is a side view of a needle-like peg according to another embodiment hereof, wherein the needle-like peg has a tapered configuration.

In another embodiment shown in FIG. 17B, pegs 1744B may be configured to pull the entire amount of filler material 120 from side port 104 when stent 100 is rolled over a peg board 1740B. More particularly, each peg 1744B is needle-like with a sharp or pointed tip 1748 that is configured to pierce into filler material 120 when stent 100 is rolled over peg board 1740B. When stent 100 is rolled over peg board 1740B, the entire amount of filler material 120 is pulled from side port 104 to fully open side port 104 and restore it to its original diameter D$_O$. Stated another way, filler material 120 would be left behind on needle-like pegs 1744B as stent 100 is continued to be rolled over peg board 1740B. The number of pegs 1744B and/or spacing between pegs 1744B thus dictate how many side ports 104 are fully opened via removal of the entire amount of filler material 120 therefrom. In the embodiment of FIG. 17B, filler material 120 sticks to needle-like pegs 1744B via friction alone. However, in another embodiment shown in FIG. 17C, needle-like pegs 1744C may include one or more barbs 1745 thereon that embed within filler material 120 after needle-like pegs 1744C pierces therethrough. Barbs 1745 improve coupling between needle-like pegs 1744C and filler material 120 when stent 100 is rolled thereover. Barbs 1745 alternatively may point or be oriented in a different direction than shown in FIG. 17C and/or have a different configuration than which is shown in FIG. 17C. In another example shown in FIG. 17D, needle-like pegs 1744D may be tapered such that a base portion 1746 thereof is thinner or narrower than the pointed tip to improve coupling between needle-like pegs 1744D and filler material 120 when stent 100 is rolled thereover.

Figure 18:
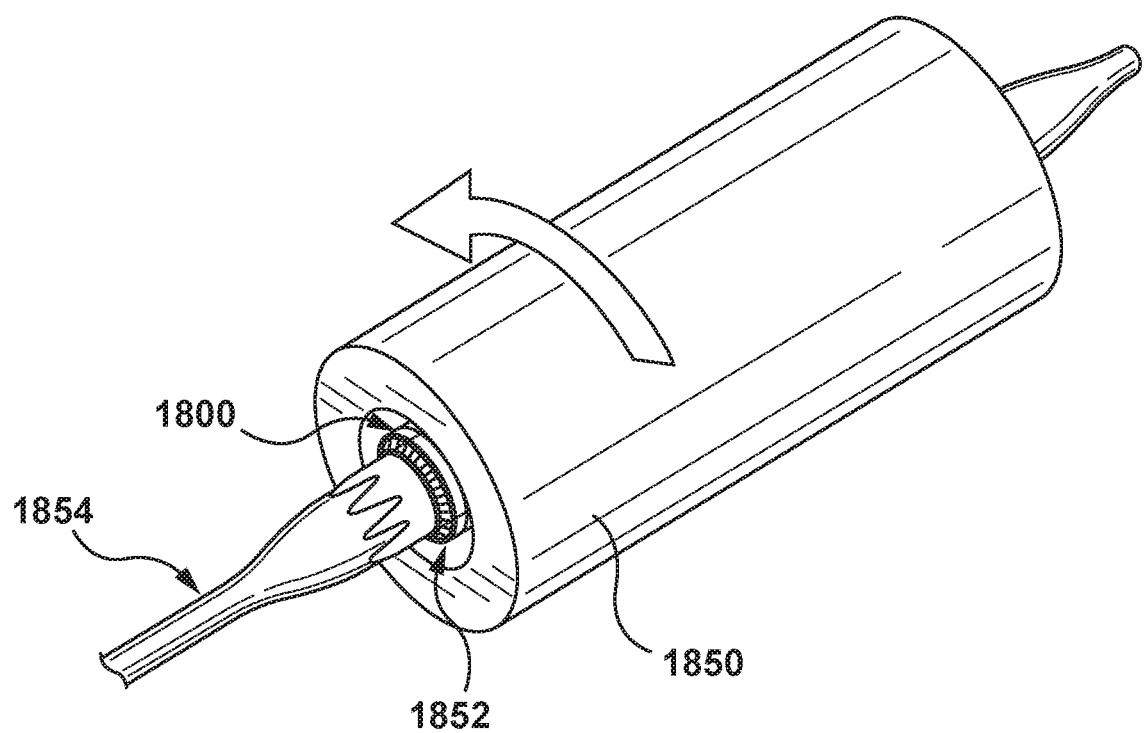
FIG. 18 is a perspective view of a roller tube that may be utilized during rolling of the drug eluting stent according to another embodiment hereof.
Figure 19:
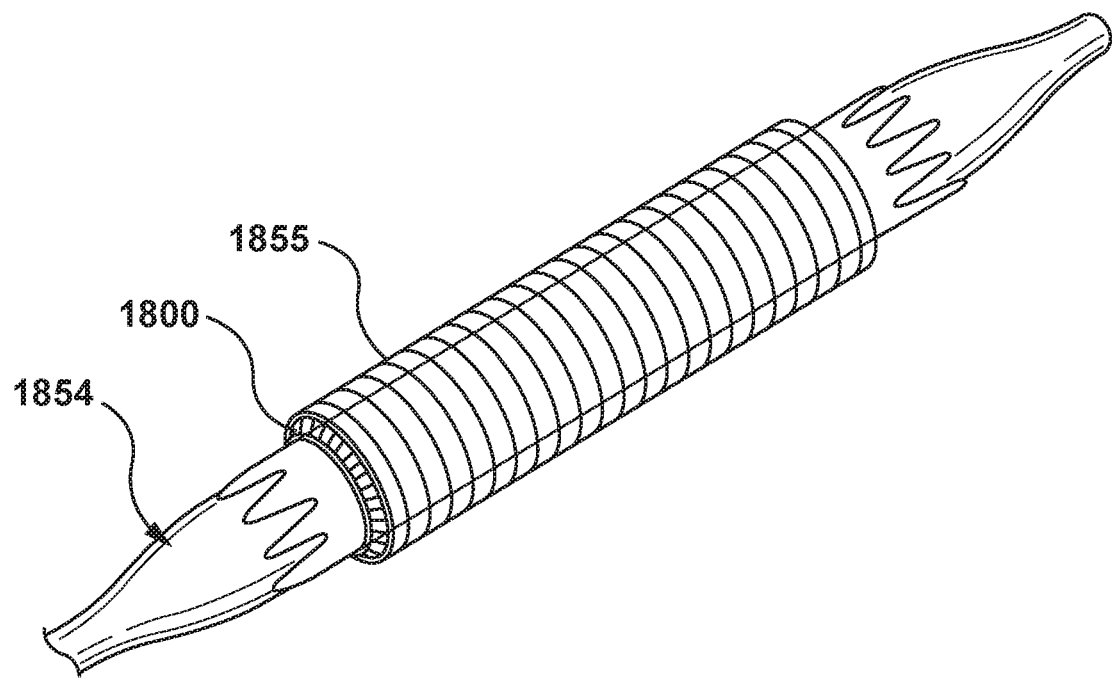
FIG. 19 is a perspective view of stent having a coating positioned thereover according to another embodiment hereof.

Similarly, a tube may be used to control or aid in mechanically breaking up filler material 120 by rolling a stent therein. For example, as shown in FIG. 18, a tube 1850 defines a chamber 1852 size to receive a stent 1800 therein. Stent 1800 may be loaded onto a balloon catheter 1854 and inserted into chamber 1852. If stent 1800 is self-expanding (and thus not pre-loaded onto a balloon catheter), the stent may be inserted into chamber 1852 via suitable stent suspension means (not shown). Stent 1800 may be rotated or spun within tube 1850 in order to mechanically breaking up filler material 120 disposed within side ports 104 of stent 1800. The surface characteristics of the inner surface of tube 1850 may be controlled and configured as desired to mechanically breaking up filler material 120, and thus spinning stent 1800 within tube 1850 protects stent 1800 from potential damage that may occur if stent 1800 were rolled over an uncontrolled surface. Further, the surface characteristics may be varied to result in different amounts of removal of filler material 120. For example, the inner surface of tube 1850 may be smooth, rough, bumpy, or otherwise configured to mechanically break up filler material 120. Although filler material 120 is described above as only being disposed within side ports 104 following manufacture, in the embodiment of FIG. 18 the entire stent 1800 is covered with a coating 1855 formed of the same material as filler material 120 as best shown in FIG. 19. FIG. 19 is a perspective view of stent 1800 having such coating 1855 positioned thereover, and stent 1800 is shown removed from tube 1850 for illustrative purposes only. Coating 1855 may remain disposed over stent 1800 after stent 1800 is spun within tube 1850 to selectively remove filler material 120 from target side ports 104 in order to customize the elution profile of stent 1800. Further, other embodiments described herein may utilize a coating formed of the same material as filler material 120 disposed over the entire length of the stent and one of the above-described methods may be utilized to selectively remove filler material 120 from target side ports 104.

Figure 20:
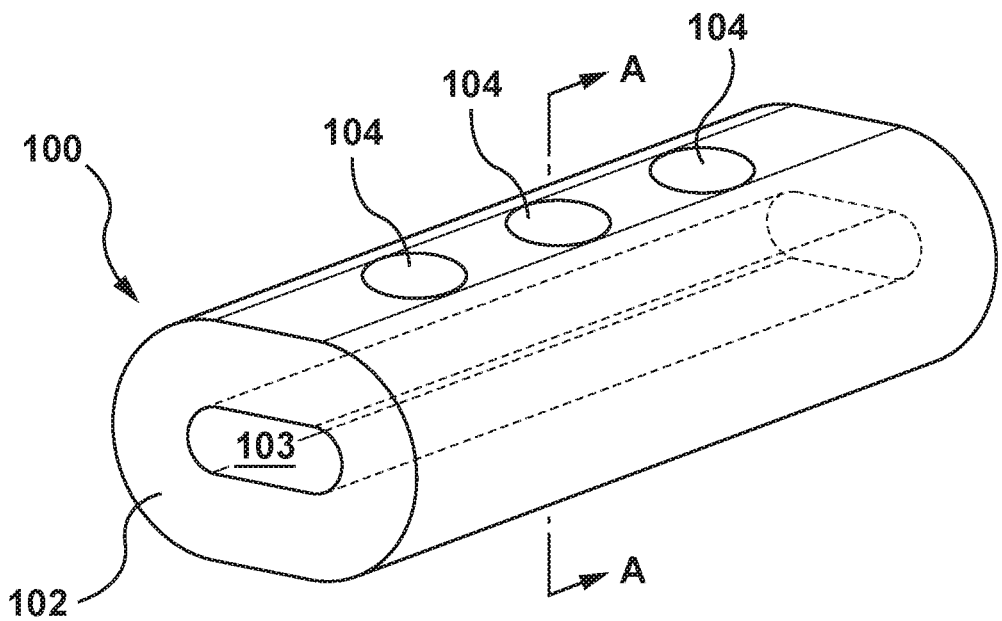
FIG. 20 is a perspective view of a portion of the drug eluting stent of FIG. 1 according to an embodiment hereof, wherein the drug eluting stent includes a plurality of elution openings that are left open or not blocked during manufacture of the stent.
Figure 20A:
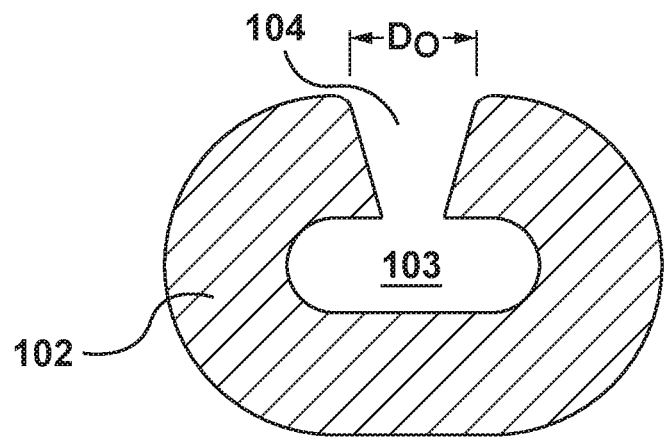
FIG. 20A is a cross-sectional view taken along line A-A of FIG. 20.
Figure 21:
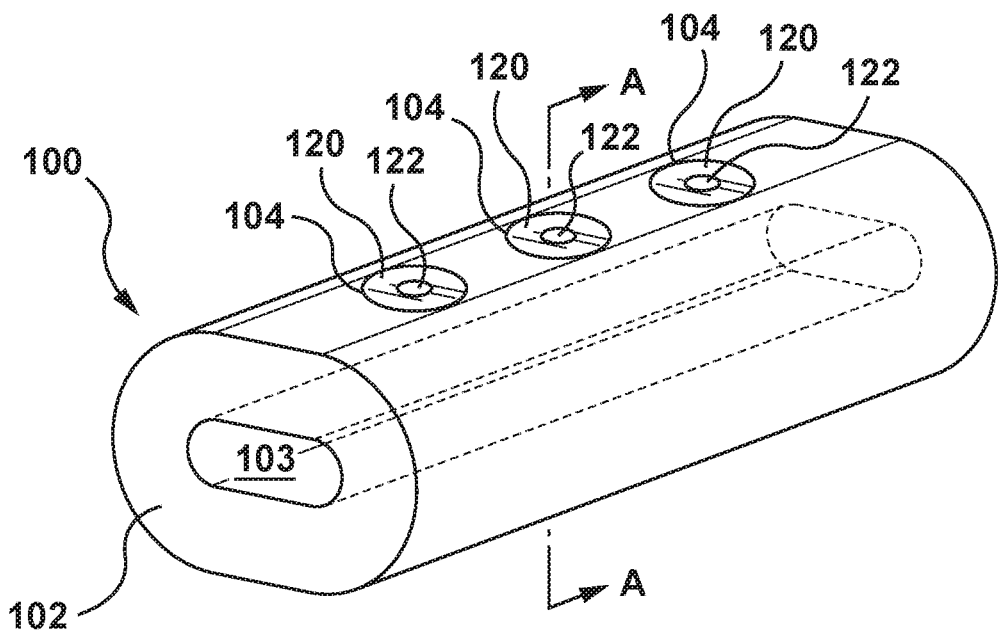
FIG. 21 is a perspective view of the portion of the drug eluting stent of FIG. 20, wherein filler material has been added to each of the plurality of side ports 104.
Figure 21A:
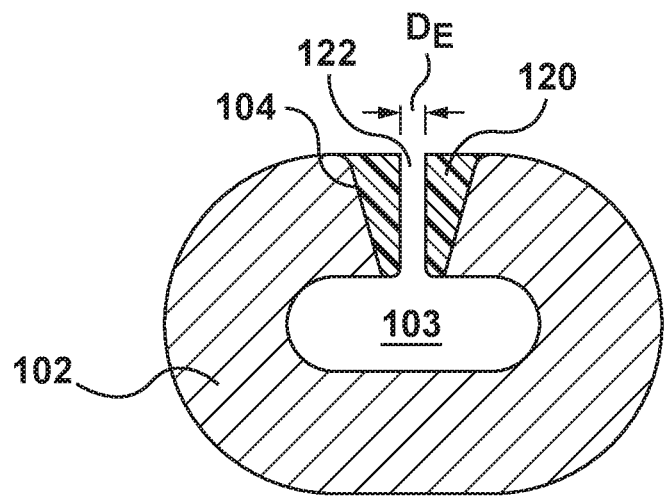
FIG. 21A is a cross-sectional view taken along line A-A of FIG. 21.

While FIGS. 4-19 relate to embodiments in which filler material is selectively removed after manufacture of stent 100 is completed in order to customize the elution profile of stent 100, FIGS. 20-21A relate to embodiments in which filler material is selectively added after manufacture of stent 100 is completed in order to customize the elution profile of stent 100. More particularly, as shown in the embodiments of FIGS. 20 and 20A, side ports 104 are left open following manufacture of stent 100, stent 100 is loaded onto a catheter, and shipped to the customer. FIG. 20 is a perspective view of a portion of stent 100 illustrating side ports 104 open after manufacture of stent 100 has been completed, and FIG. 20A is a cross-sectional view taken along line A-A of FIG. 20. As described above, during manufacture an original diameter $D_O$ (shown on FIG. 20A, as well as FIG. 2A and FIG. 3) of side ports 104 is sized for a maximum or maximized elution rate of therapeutic substance or drug 112 from stent 100. The original diameter $D_O$ of side ports 104 may be modified after manufacture of stent 100 has been completed in order to customize the elution profile of stent 100. Stated another way, the elution profile of a standard or an off-the-shelf product may be modified by a physician by adding filler material 120 to side ports 104 in order to decrease the effective diameter $D_E$ of select side ports 104 and thereby meet individual requirements of a specific patient. By way of example only, the step of adding filler material 120 to side ports 104 in order to modify the elution profile of stent 100 may be performed by a physician in a catheterization laboratory or cath lab. As with embodiments described above, the number (quantity) and/or size (diameter) of side ports 104 can be modified in the cath lab by the physician in order to vary the quantity and/or rate of therapeutic substance or drug 112 being eluted out of side ports 104 and thereby customize the elution profile of stent 100.

At least one side port 104 is at least partially filled with filler material 120 to form channel 122 with the filler material as shown in FIGS. 21 and 21A. FIG. 21 is a perspective view of a portion of stent 100 illustrating side ports 104 after the addition of filler material 120 to each side port 104, and FIG. 21A is a cross-sectional view taken along line A-A of FIG. 21. As described above, in an embodiment, filler material 120 is a bioabsorbable or biodegradable polymer such as but not limited to polylactic acid (PLLA), polycaprolactone, and aliphatic polyesters. In another embodiment, filler material 120 is magnesium. In another embodiment, filler material 120 is a biostable material such as but not limited to polyethylene, polyurethane, and polypropylene. Each channel 122 extends through the thickness of filler material 120 such that each channel 122 is in fluid communication with lumenal space 103 of hollow strut 102 to permit elution of therapeutic substance or drug 112 from lumenal space 103 through channel 122 formed within side port 104. Each channel 122 forms the effective diameter $D_E$ of its respective side port 104. Relative to the state of FIGS. 20 and 20A in which side port 104 is open, the addition of filler material 120 thereby decreases effective diameter $D_E$ of the respective side port 104 and customizes an elution profile of the stent. The elution rate of stent 100 is controlled by effective diameters $D_E$ of side ports 104 which can be controlled by adding or inserting a predetermined or select amount of filler material 120. The amount of filler material 120 added or inserted into each side port 104 may vary to create a customizable drug elution profile and be tailored to the patient requirements.

In an embodiment, the physician adds or inserts filler material 120 into side ports 104 by submersing stent 100 into a bath of filler material 120 in its liquid form. Stent 100 is fully or partially submersed into the bath of filler material 120 in its liquid form such that the same amount of filler material 120 is added to each side port 104 and thus each side port 104 has the same effective diameter $D_E$ as shown in the embodiment of FIGS. 21 and 21A. This is desirable when a consistent elution profile along the entire stent length is required. However, in another embodiment, the quantity of side ports 104 and/or the relative size of channels 122 may be varied along stent 100 in order to vary the quantity and/or rate of therapeutic substance or drug 112 being eluted side ports 104 and thereby customize the elution profile of stent 100 as described above with respect to FIGS. 10 and 11. Adding different amounts of filler material 120 may be accomplished by manually applying a filler material 120 in its liquid form via a sponge, spray, brush, or another suitable utensil. Adding different amounts of filler material 120 form channels 122 to have different diameters so that side ports 104 have different effective diameters $D_E$. Further, the physician may desire to completely block or plug select side ports 104 with filler material 120 while other side ports 104 are only partially blocked to varying degrees as desired. After insertion into the patient, filler material 120 prevents or slows the rate at which therapeutic drug 120 egresses or elutes from channels 122/side ports 104.

In an embodiment, the physician adds or inserts filler material 120 into side ports 104 by 3D printing filler material 120. The methods as described herein are methods for adding or inserting filler material 120 into side ports 104 using "additive manufacturing" or "three-dimensional printing" (or "3D printing") or "rapid prototyping". The terms "additive manufacturing" or "three-dimensional printing" or "rapid prototyping" refer to a process of making a three-dimensional solid object of virtually any shape from a digital model. 3D printing is achieved using an additive process, where successive layers of material are laid down in different shapes. The terms, as used herein, may refer to methods such as, but not limited to, selective laser melting (SLM), direct metal laser sintering (DMLS), selective laser sintering (SLS), fused deposition modeling (FDM), and stereolithography (SLA). Exemplary 3D printers or additive manufacturing machines are described in more detail within U.S. patent application Ser. Nos. 15/491,138 and 15/491,170, each of which is herein incorporated by reference in their entirety. Further, any type of 3D printer or additive manufacturing machine that can print the materials described herein may be used.

A 3D printer (not shown) may be pre-programmed with a plurality of elution profiles based on a number of clinical and/or animal trials. More particularly, the 3D printer receives a dataset relating to the plurality of pre-programmed elution profiles. In particular, the dataset is information regarding the patterns and dimensions for filler material 120 within side ports 104 which the 3D printer can form the pre-programmed elution profile. For example, the dataset may cause the 3D printer to fill one or more side ports 104 a predetermined percentile amount with filler material 120. The dataset may also or alternatively cause the 3D printer to completely block or plug a predetermined pattern of side ports 104 with filler material 120. For example, and not by way of limitation, the dataset may be a 3D printable file such as an STL file. STL (STereoLithography) is a file format native to the stereolithography CAD software created by 3D Systems. STL is also known as Standard Tessellation Language. This file format is supported by many software packages for use in 3D printing. The physician would be allowed to choose one of these pre-programmed elution profiles, and the 3D printer will fill side ports 104 according to the selected pre-programmed elution profile. Side ports 104 of stent 100 would be automatically filled according to the selected pre-programmed elution profile. The 3D printer may include a fixture for holding stent 100 within the 3D printer and rotating stent 100 to ensure that all side ports 104 are filled as required by the selected pre-programmed elution profile.

In an embodiment, the 3D printer may be programmed such that the physician can choose to interpolate between pre-programmed elution profiles with the qualification that there is no clinical data for any of the elution rates which are not pre-programmed. More particularly, machine software of the 3D printer may be configured to interpolate between pre-programmed elution profiles. The instructions for use for the 3D printer should include instructions that only the pre-programmed elution profiles have been verified by clinical and/or animal trials.

In another embodiment hereof, rather than modifying an effective diameter of a side port in order to customize an elution profile of the stent, the amount of therapeutic substance or drug 112 may be modified in order to customize an elution profile of the stent. During manufacture of stent 100, lumenal space 103 is filled to maximum capacity with therapeutic substance or drug 112, loaded onto a catheter, and shipped to the customer. When a lower elution profile is required, the physician can modify the elution profile of the stent by washing or soaking the stent in a liquid for a pre-determined time to reduce the amount of therapeutic substance or drug 112 disposed within lumenal space 103. By altering the amount of therapeutic substance or drug 112 present in stent 100, the elution profile of stent 100 can be tailored to suit the individual needs of the patient.

Figure 26:
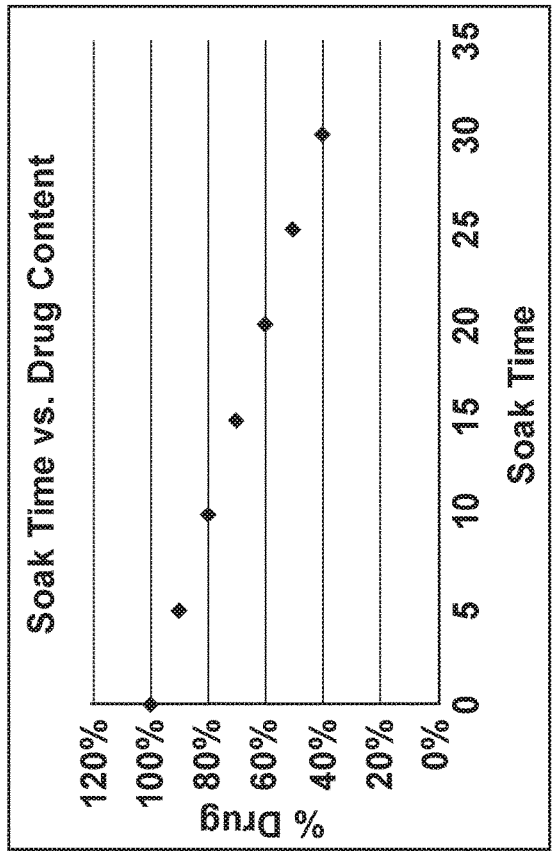
FIG. 26 illustrates a chart depicting the relationship between drug content reduction and the amount of soak time.
Figure 25:
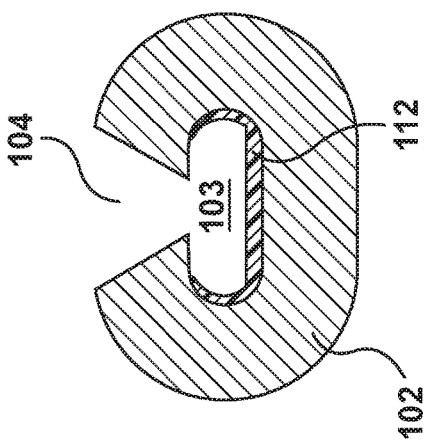
FIG. 25 illustrates a cross-sectional view of the hollow strut of the stent of FIG. 22, wherein only a small amount of therapeutic drug remains within the lumenal space of the hollow strut following an additional second predetermined elapsed time period.
Figure 24:
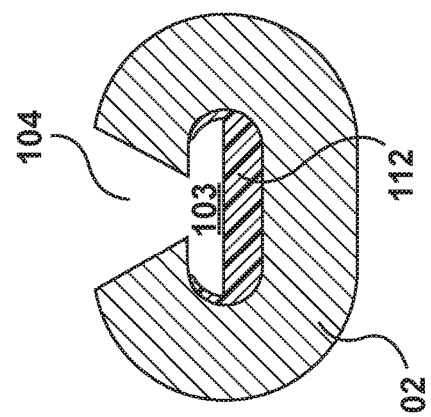
FIG. 24 illustrates a cross-sectional view of the hollow strut of the stent of FIG. 22, wherein the lumenal space of the hollow strut is only partially filled with the therapeutic drug after removal of the therapeutic drug following a first predetermined elapsed time period.
Figure 23:
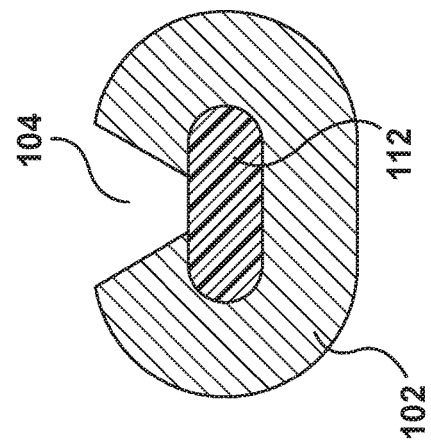
FIG. 23 illustrates a cross-sectional view of the hollow strut of the stent of FIG. 22, wherein the lumenal space of the hollow strut is filled to maximum capacity with the therapeutic drug.
Figure 22:
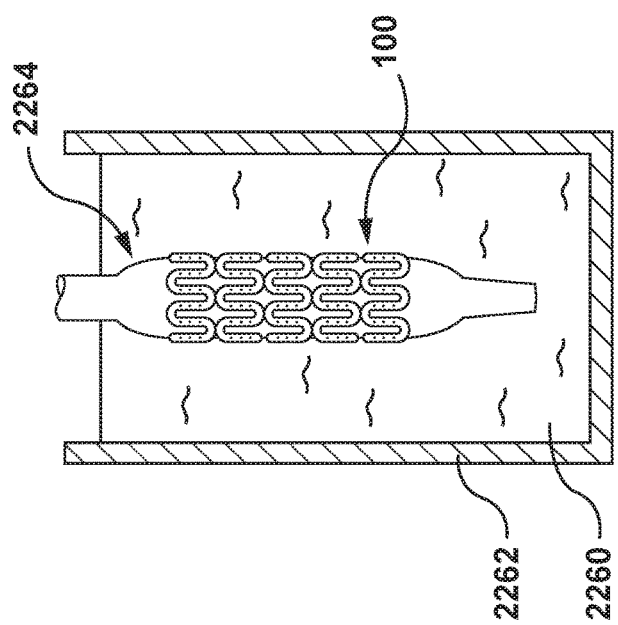
FIG. 22 illustrates a method of removing at least a portion of a therapeutic drug from a lumenal space of the hollow strut that forms the stent of FIG. 1 according to another embodiment hereof, wherein the method includes a submersing the drug eluting stent into a bath of a liquid.

For example, as shown in FIG. 22, stent 100 disposed on a balloon catheter 2264 is lowered into an open-ended container 2262 such that stent 100 is fully or partially submersed into a bath or reservoir of liquid 2260 which will absorb or remove therapeutic substance or drug 112 from lumenal space 103 by a time-dependent amount. In an embodiment, liquid 2260 is a saline solution. If stent 100 is self-expanding (and thus not pre-loaded onto a balloon catheter), the stent may be lowered into open-ended container 2262A via suitable stent suspension means (not shown). After being fully or partially submersed into a bath or reservoir of liquid 2260, the amount of therapeutic substance or drug 112 which is removed or absorbed by liquid 2260 varies depending on the length of time that stent 100 is fully or partially submersed within liquid 2260. In addition, the amount of therapeutic substance or drug 112 which is removed or absorbed by liquid 2260 varies depending on the type of liquid utilized. Stated another way, different exposure times and/or different liquids used controls the amount of therapeutic substance or drug 112 removed. FIGS. 23-25 illustrate cross-sectional views of a hollow strut 102 during soaking in order to remove at least a portion of therapeutic substance or drug 112 following various predetermined elapsed time periods. FIG. 23 illustrates lumenal space 103 of hollow strut 102 filled to maximum capacity with therapeutic substance or drug 112. In FIG. 24, following a first predetermined elapsed time period, about half of therapeutic substance or drug 112 has been removed from lumenal space 103 and thus results in a relatively slower elution profile of stent 100. In general, larger amounts of therapeutic substance or drug 112 generally permit a faster elution rate and smaller amounts of therapeutic substance or drug 112 generally provide a slower elution rate. In FIG. 25, additional therapeutic substance or drug 112 has been absorbed or removed from lumenal space 103 by liquid 2260 following an additional second elapsed time period to result in an even slower elution rate. FIG. 26 illustrates a chart depicting the relationship between drug content reduction and the amount of soak time. By controlling the amount of the time that stent 100 is soaked in liquid 2260, the amount of therapeutic substance or drug 112 present in lumenal space 103 of hollow strut 102 can be tailored. As such, the physician can customize or tailor the elution profile of stent 100 after manufacture of stent 100 is completed by controlling the amount of therapeutic substance or drug 112 present in lumenal space 103 of hollow strut 102.

For all methods of customizing an elution profile, stent 100 may be shipped with instructions for use for how the elution profile thereof may be customized or tailored by the physician. The instructions for use describe at least the method steps for removing or adding filler material 120 to side ports 104 as described in the embodiments above. The instructions for use may include only one type of method for customizing the elution profile of stent 100 (i.e., according to one of the methods described herein) or the instructions for use may include more than one method for customizing the elution profile. In addition, the instructions for use may also include known or established elution profiles which have been verified by clinical and/or animal trials or mathematical models. More particularly, the instructions for use may include directives on how much filler material 120 is to be located within each side port 104 in order to result in the known or established elution profiles. The physician may use such directives when selecting a customized elution profile for stent 100. Such directives provide precise guidance to the physician as to which side ports should be plugged and which side ports should be open, and dimensions for the effective diameter of each side port that is open.

While various embodiments of the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments. It will also be understood that each feature of each embodiment discussed herein, and of each reference cited herein, can be used in combination with the features of any other embodiment. Furthermore, there is no intention to be bound by any expressed or implied theory presented in the preceding technical field, background, brief summary or the detailed description. All patents and publications discussed herein are incorporated by reference herein in their entirety.

What is claimed is:

1. A method of customizing an elution profile of a stent after manufacture of the stent has been completed, the method comprising the steps of:
   providing the stent, wherein the stent includes a drug formulation disposed within a lumenal space of a hollow strut that forms the stent and a plurality of side ports for eluting the drug formulation within the lumenal space of the hollow strut that forms the stent; and
   modifying an effective diameter of at least one side port of the plurality of side ports of the stent in order to customize an elution profile of the stent, wherein the step of modifying the effective diameter of at least one side port of the plurality of side ports of the stent occurs after the step of providing the stent and prior to use of the stent in vivo.

2. The method of claim 1, wherein the step of modifying the effective diameter of at least one side port includes modifying the effective diameter of each of the plurality of side ports of the stent.

3. The method of claim 1, wherein the step of modifying the effective diameter of at least one side port includes not modifying the effective diameter of at least one side port of the plurality of side ports of the stent.

4. The method of claim 1, wherein the plurality of side ports are open following the step of providing the stent and the step of modifying the effective diameter of at least one side port includes at least partially filling the at least one side port with a filler material to decrease the effective diameter of the at least one side port.

5. The method of claim 4, wherein the filler material is a bioabsorbable polymer.

6. The method of claim 4, wherein a 3D printer is used in at least partially filling the at least one side port with a filler material.

7. The method of claim 6, wherein the 3D printer fills a predetermined percentile amount of the at least one side port with the filler material.

8. The method of claim 6, wherein the 3D printer completely blocks a predetermined pattern of holes of the plurality of side ports with the filler material.

9. The method of claim 1, wherein the plurality of side ports are completely blocked with a filler material during the manufacture of the stent and wherein the step of modifying the effective diameter of at least one side port includes removing at least a portion of the filler material to increase the effective diameter of the at least one side port.

10. The method of claim 9, wherein removing at least a portion of the filler material is achieved by exposing the filler material to a reagent for a predetermined amount of time to dissolve the filler material.

11. The method of claim 10, wherein the reagent is an acid or an etching agent.

12. The method of claim 9, wherein removing at least a portion of the filler material is achieved by exposing the filler material to light for a predetermined amount of time to chemically break down the filler material.

13. The method of claim 12, wherein a stencil is positioned over the at least one side port while exposing the filler material to light for the predetermined amount of time.

14. The method of claim 9, wherein removing at least a portion of the filler material is achieved by rolling the stent to mechanically break down the filler material.

15. The method of claim 14, wherein rolling the stent includes rolling the stent over a board with pegs thereon.

16. The method of claim 14, wherein rolling the stent includes spinning the stent within a tube that is disposed over the stent.

17. The method of claim 9, wherein removing at least a portion of the filler material is achieved by exposing the filler material to heat for a predetermined amount of time to melt the filler material.

18. A method of customizing an elution profile of a stent after manufacture of the stent has been completed, the method comprising the steps of:
   providing the stent, wherein the stent includes a drug formulation disposed within a lumenal space of a hollow strut that forms the stent and a plurality of side ports for eluting the drug formulation within the lumenal space of the hollow strut that forms the stent, the plurality of side ports being completely blocked with a filler material; and
   removing at least a portion of the filler material from at least one side port of the plurality of side ports to form a channel through the filler material, the channel thereby forming an effective diameter of the at least one side port, to thereby increase the effective diameter of the at least one side port and customize an elution profile of the stent, wherein the step of removing at least the portion of the filler material from at least one side port of the plurality of side ports occurs after manufacture of the stent has been completed and prior to use of the stent in vivo.

19. A method of customizing an elution profile of a stent after manufacture of the stent has been completed, the method comprising the steps of:
   providing the stent, wherein the stent includes a drug formulation disposed within a lumenal space of a hollow strut that forms the stent and a plurality of side ports for eluting the drug formulation within the lumenal space of the hollow strut that forms the stent, the plurality of side ports being open; and
   at least partially filling at least one side port of the plurality of side ports of the stent with a filler material to form a channel with the filler material, the channel thereby forming an effective diameter of the at least one side port, to thereby decrease the effective diameter of the at least one side port and customize an elution profile of the stent, wherein the step of at least partially filling at least one side port of the plurality of side ports occurs after the step of providing the stent and prior to use of the stent in vivo.

20. A method of customizing an elution profile of a stent after manufacture of the stent has been completed, the method comprising the steps of:

providing the stent, wherein the stent includes a drug formulation disposed within a lumenal space of a hollow strut that forms the stent and a plurality of side ports for eluting the drug formulation within the lumenal space of the hollow strut that forms the stent, the lumenal space of the hollow strut being filled to a maximum capacity with the drug formulation following the manufacture of the stent; and soaking the stent within a liquid to remove at least a portion of the drug formulation from the lumenal space of the hollow strut to thereby customize an elution profile of the stent, wherein the step of soaking the stent within the liquid occurs after manufacture of the stent has been completed and prior to use of the stent in vivo.

\* \* \* \* \*